United States Patent [19]

Vogt et al.

[11] 4,051,248

[45] Sept. 27, 1977

[54] 1,3,8-TRIAZASPIRO(4.5)DECAN-4-ONE DERIVATIVES

[75] Inventors: B. Richard Vogt, Yardley, Pa.; David A. Cullison, Princeton, N.J.

[73] Assignee: E. R. Squibb & Sons, Inc., Princeton, N.J.

[21] Appl. No.: 688,438

[22] Filed: May 20, 1976

Related U.S. Application Data

[63] Continuation-in-part of Ser. No. 595,947, July 14, 1975, abandoned.

[51] Int. Cl.² ............... C07D 471/10; A61K 31/445
[52] U.S. Cl. ........................... 424/267; 260/293.62
[58] Field of Search .......... 260/293.62, 293.6, 293.66; 424/267

[56] References Cited

U.S. PATENT DOCUMENTS

| | | | |
|---|---|---|---|
| 3,917,598 | 11/1975 | Maruyama et al. | 260/268 PH |
| 3,922,266 | 11/1975 | Katsube et al. | 260/240 J |
| 3,923,794 | 12/1975 | Maruyama et al. | 260/240 A |
| 3,925,387 | 12/1975 | Maruyama et al. | 260/268 PH |

*Primary Examiner*—G. Thomas Todd
*Attorney, Agent, or Firm*—Lawrence S. Levinson; Merle J. Smith; Donald J. Barrack

[57] ABSTRACT

Compounds having the structure

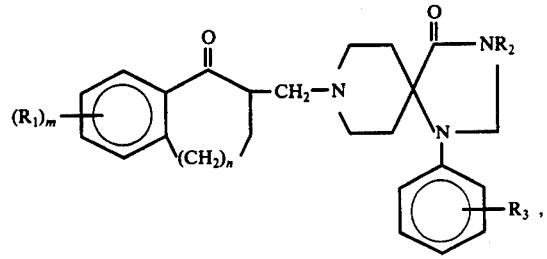

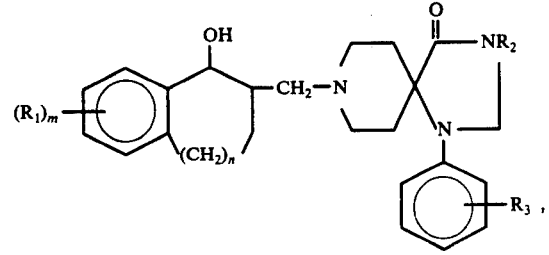

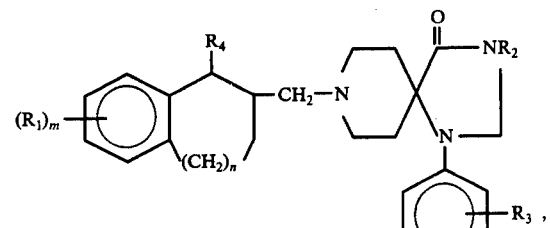

and

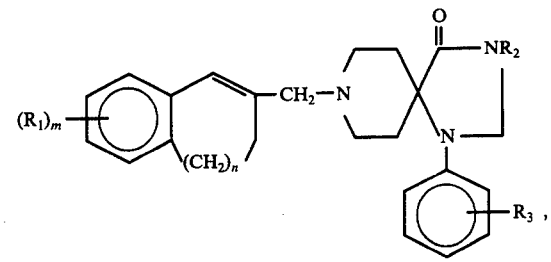

and the pharmaceutically acceptable salts thereof, wherein $R_1$ is hydrogen, halogen, hydroxy, alkanoyloxy, alkoxy, alkylthio, alkyl or trifluoromethyl; $R_2$ is hydrogen, alkyl or alkenyl; $R_3$ is hydrogen, halogen or alkyl; $R_4$ is formyloxy or alkanoyloxy; $m$ is 1 or 2; and $n$ is 0, 1 or 2; have useful physiological activity.

16 Claims, No Drawings

1,3,8-TRIAZASPIRO(4.5)DECAN-4-ONE DERIVATIVES

This application is a continuation-in-part of copending United States patent application Ser. No. 595,947, filed July 14, 1975, and now abandoned.

BRIEF DESCRIPTION OF THE INVENTION

Compounds having the structure

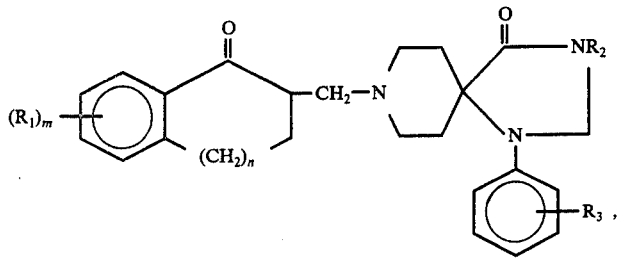

Ia

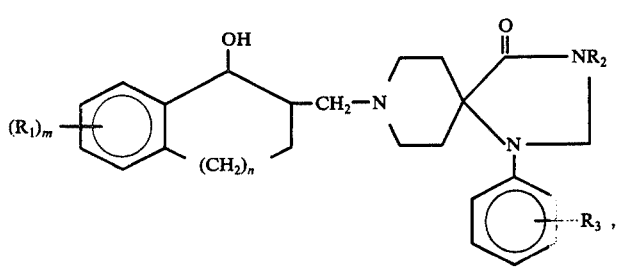

Ib

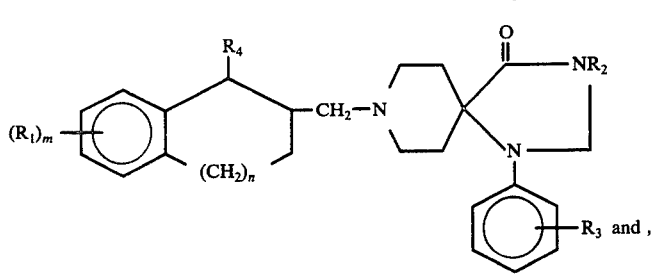

Ic

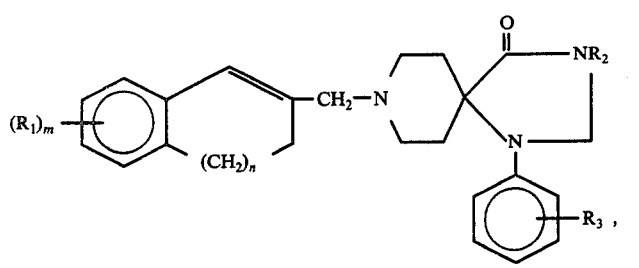

Id and the pharmaceutically acceptable salts thereof, have useful physiological activity. In formula I, and throughout the specification, the symbols are as defined below:
  $R_1$ can be hydrogen, halogen, hydroxy, alkanoyloxy, alkoxy, alkylthio, alkyl or trifluoromethyl;
  $R_2$ can be hydrogen, alkyl or alkenyl;
  $R_3$ can be hydrogen, halogen or alkyl;
  $R_4$ can be formyloxy or alkanoyloxy;
  $m$ is 1 or 2; and
  $n$ is 0, 1 or 2.

The term "alkyl," as used throughout the specification, refers to a straight or branched chain alkyl group having 1 to 4 carbon atoms.

The terms "alkoxy" and "alkylthio", as used throughout the specification, refer to groups having the formula Y—O— and Y—S—, respectively, wherein Y is alkyl as defined above.

The term "alkenyl", as used throughout the specification, refers to a hydrocarbon group having 2 to 4 carbon atoms and containing a single carbon to carbon double bond.

The term "alkanoyloxy", as used throughout the specification, refers to a group having the formula

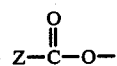

wherein Z is alkyl having 1 to 10 carbon atoms.

The term "halogen," as used throughout the specification, refers to fluorine, chlorine, bromine and iodine; fluorine, chlorine and bromine are the preferred halogens.

DETAILED DESCRIPTION OF THE INVENTION

The compounds of formulas Ia, Ib, Ic and Id, and the pharmaceutically acceptable salts thereof, are physiologically active substances which possess useful central nervous system depressant and neuroleptic activity. They can be used as major tranquilizers in the treatment of mammalian species such as rats, dogs, monkeys, etc. For this purpose these compounds may be incorporated in a conventional dosage form such as tablet, capsule, injectable or the like, along with the necessary carrier material, excipient, lubricant, buffer or the like, for oral or parenteral administration in single or divided doses of about 0.5 to 100 mg/kg/day, preferably about 3 to 15 mg/kg, two to four times daily.

The neuroleptic activity of the compounds of the invention is illustrated by their ability to decrease avoidance behavior in rats and monkeys according to procedures similar to that of Tenen [cf. Psychon. Sci., 6, 407-408 (1966)].

The compounds of formula I$a$ can be prepared using as starting materials compounds having the formula

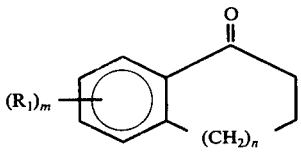

Using the well-known Mannich reaction, a compound of formula II can be reacted with a dialkylamine (preferably in the form of its hydrohalide salt), and formaldehyde or paraformaldehyde, to yield a Mannich base ketone having the formula

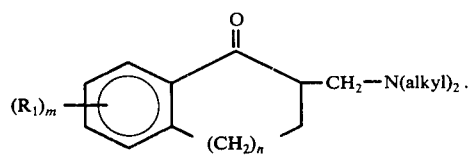

Reaction of a Mannich base ketone intermediate of formula III (preferably in the form of its hydrohalide salt) with a compound having the structure

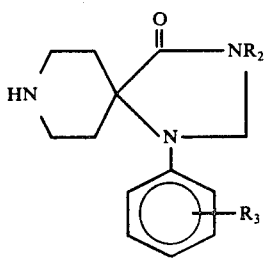

yields a compound of formula I$a$. The reaction can be run in an organic solvent such as ethanol, at a temperature of 0° to 100° C for 1 hour to 72 hours.

Alternatively, the compounds of formula I$a$ can be prepared in a single step Mannich reaction by reacting a compound of formula II with a compound of formula IV (preferably in the form of its hydrohalide salt), and formaldehyde or paraformaldehyde.

The compounds of formula I$a$, in addition to possessing the pharmaceutical activities described above, are useful intermediates for the preparation of the compounds of formulas I$b$, I$c$ and I$d$.

The 1-oxo compounds of formula I$a$ an be selectively reduced (chemically or by catalytic means) to form the corresponding 1-hydroxy compound of formula I$b$. Exemplary of the reduction processes is the reaction of a co npound of formula I$a$ (or its hydrohalide salt) with sodium borohydride in a lower alkanol solvent, optionally in the presence of water. A second process comprises reacting a compound of formula I$a$ (or its hydrohalide salt) with gaseous hydrogen in the presence of a catalyst, e.g., palladium or platinum oxide, optionally in the presence of ferric chloride, in a solvent, e.g., water, a lower alkanol, or an ether such as tetrahydrofuran or dioxane.

Other chemical reducing agents which can be used in the process of this invention include lithium trialkylborohydrides and dialkylboranes.

The compounds of formula I$b$, in addition to possessing the pharmaceutical activities described above, are useful intermediates for the preparation of the compounds of formulas I$c$ and I$d$.

The 1-hydroxy compounds of formula I$b$ can be converted to the esters of formula I$c$ by reaction with the appropriate acid, acyl halide or acid anhydride.

The 1-hydroxy compounds of formula I$b$ can also be converted to compounds of formula I$d$ by dehydration in the presence of a mineral acid such as hydrochloric acid or sulfuric acid, or a strong organic acid such as p-toluenesulfonic or methanesulfonic acid, or by other methods wellknown to those skilled in the art (cf. "Survey of Organic Syntheses," C. A. Buehler and D. E. Pearson, Wiley-Inter-science, New York, 1970, pp. 71-75). For example, the dehydration reaction may be carried out with sulfuric acid in the presence of an organic solvent such as acetic acid at a temperature of 0° to 100° C for 0.5 to 48 hours.

An alternative procedure for obtaining compounds of formula I$d$ uses as starting materials compounds having the formula

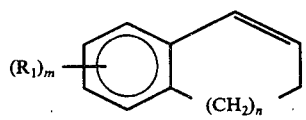

wherein R$_1$ is preferably other than hydroxy.

Reacting compounds of formula V with paraformaldehyde and hydrobromic acid or, preferably, hydrochloric acid yields a compound of formula VI

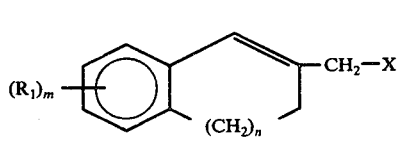

wherein X is bromine or chlorine. The reaction can be run at a temperature of 40° to 160° C for 0.5 hour to 48 hours. Reaction of the dihydro compound of formula VI with a compound of formula IV yields a compound of formula I$d$. The reaction can be run in the presence of a hydrogen halide acceptor such as sodium or potassium carbonate or bicarbonate in an organic solvent under an inert gas such as nitrogen. The reaction is carried out at from about 0° to about 200° C, preferably from about 50° to about 150° C, until a significant amount of end product is obtained, typically, for from about 0.5 to about 72 hours, preferably from about 1 to about 24 hours.

Typical organic solvents which may be used in the above reaction include alkanols of 1–5 carbons such as methanol, ethanol, t-butanol, n-butanol and the like; ethers of 4-12 carbons such as ethyl ether, tetrahydrofuran, dioxane, diphenyl ether, 1,2-dimethoxyethane and the like; aromatic hydrocarbons of 6-10 carbons such as benzene, toluene, xylene and the like; di-, tri- and tetrachlorohydrocarbons of 1–4 carbons such as methylene chloride, chloroform, dichloroethane, tetrachloroethane and the like; N,N-dialkylformamides, N,N-dialkyl alkanoyl amides wherein the alkyl and alkanoyl radicals have 1–4 carbons, such as dimethylformamide, dimethylacetamide and the like; dialkyl sulfoxides of 3–5 carbons such as dimethyl sulfoxide and the like; hexamethylphosphorous triamide, dialkylketones of 3–9 carbons such as acetone, methyl ethyl ketone and the like.

The dihydro compound of formula VI can also be reacted with a disubstituted piperidine having the formula

VII

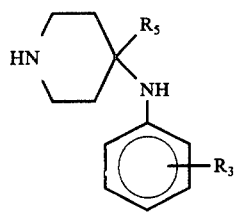

wherein $R_5$ is cyano or carbamoyl to give a compound having the formula

VIII

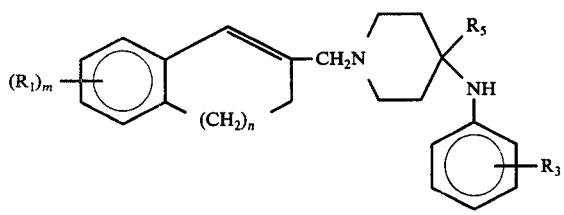

using the same conditions and reagents as in the preceding reaction.

Another synthesis of compounds of formula VIII starts with the reaction of compounds of formula VI with 4-piperidone or its hydrate or 4-hydroxy alkali metal sulfite derivatives to give compounds having the formula

IX

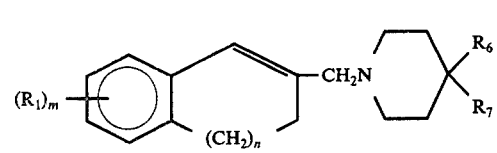

wherein $R_6$ is hydroxy and $R_7$ is hydroxy or alkali metal sulfite or $R_6$ and $R_7$ taken together are a keto group. The same conditions and reagents are employed here as above.

Compounds of formula IX can be reacted with a substituted aniline, bearing a substituent as defined for $R_3$, and an alkali metal cyanide to give a compound of formula VIII wherein $R_5$ is cyano. The reaction can be run in an aqueous organic solvent such as aqueous ethanol, at a temperature of 0° C to 100° C for 1 hour to 72 hours.

Compounds of formula VIII wherein $R_5$ is cyano can be hydrolyzed, preferably with acid, to yield a compound of formula VIII wherein $R_5$ is carbamoyl. Typical acids useful for the hydrolysis reaction include strong aqueous inorganic acids such as hydrochloric, phosphoric or sulfuric acid. The reaction can be run at a temperature of 25° to 150° C for 0.4 hours to 48 hours.

Compounds of formula VIII wherein $R_5$ is carbamoyl can be cyclized by treatment with formamide, in the optional presence of an inorganic acid such as sulfuric acid, to give a compound of formula I$d$ wherein $R_2$ is hydrogen. The reaction can be run at a temperature of 50° to 200° C for 0.5 hour to 48 hours.

Another procedure for obtaining compounds of formula I$d$, wherein $R_1$ is other than alkanoyloxy and $R_2$ is hydrogen, comprises reacting compounds of formula VIII, wherein $R_4$ is carbamoyl, with a trialkoxymethane, such as triethoxy or trimethoxymethane, to give a compound having the formula

X

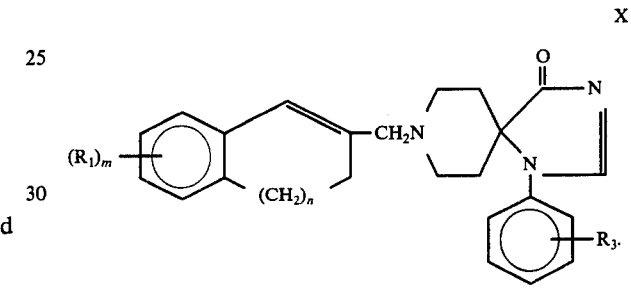

The reaction can be run in an organic solvent such as toluene in the presence of acetic acid at a temperature of 50° C to 150° C for 0.5 hour to 72 hours.

The compounds of formula X can be reduced with mixed metal hydrides such as lithium aluminum hydride or sodium aluminum hydride to give a product of formula I$d$ wherein $R_1$ is other than alkanoyloxy and $R_2$ is hydrogen. The reaction can be run in organic solvents such as benzene and tetrahydrofuran at a temperature of 25° C to reflux for 0.5 hour to 48 hours.

Another procedure for the synthesis of compounds of formula I$d$, wherein $R_2$ is hydrogen, uses as starting materials the compounds of formula III which are reacted (preferably in the form of the hydrohalide salt) with compounds of formula VII wherein $R_5$ is cyano or carbamoyl to yield compunds having the formula

XI

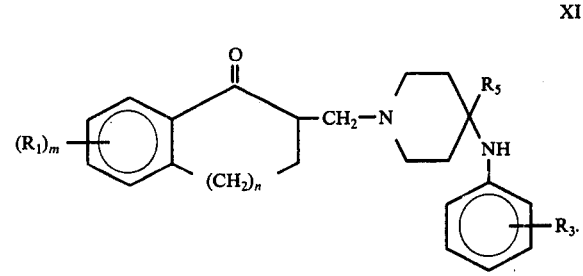

The reaction can be run in an organic solvent such as ethanol, at a temperature of 0° to 100° C for 1 hour to 72 hours.

The 1-oxo compounds of formula XI are selectively reduced (chemically or by catalytic means) to form the corresponding 1-hydroxy compound having the formula

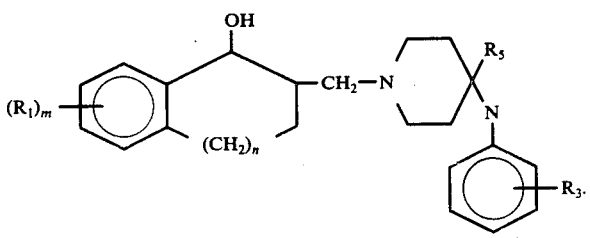

XII

Exemplary of the reduction processes is the reaction of a compound of formula XI (or its hydrohalide salt) with sodium borohydride in a lower alkanol solvent, optionally in the presence of water. A second process comprises reacting a compound of formula XI (or its hydrohalide salt) with gaseous hydrogen in the presence of a catalyst, e.g., palladium or platinum oxide, optionally in the presence of ferric chloride, in a solvent, e.g., water, a lower alkanol, or an ether such as tetrahydrofuran or dioxane.

Other chemical reducing agents which can be used in the process of this invention include lithium trialkylborohydrides and dialkylboranes.

Compounds of formula XII wherein $R_5$ is cyano can be hydrolyzed, preferably with acid, to yield a compound of formula VIII wherein $R_5$ is carbamoyl. Typical acids include strong aqueous inorganic acids such as hydrochloric, phosphoric or sulfuric acid. The reaction can be run at a temperature of 25° to 150° C for 0.4 hour to 48 hours.

Compounds of formula XII wherein $R_5$ is carbamoyl can be cyclized by treatment with formamide, in the optional presence of an inorganic acid such as sulfuric acid, to give a compound of formula I wherein $R_2$ is hydrogen. The reaction can be run at a temperature of 50° to 200° C for 0.5 hour to 48 hours.

An alternate procedure for obtaining compounds of formula Id comprises first carboxylating a compound of formula V to yield a compound having the formula

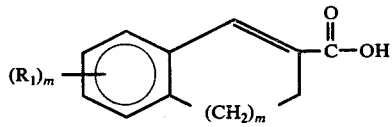

XIII

Exemplary of the carboxylation procedures is the reaction of an olefin of formula V with a halosulfonylisocyanate, followed by treatment with an acid, preferably a mineral acid such as hydrochloric acid.

The acid of formula XIII can be converted to an amide having the formula

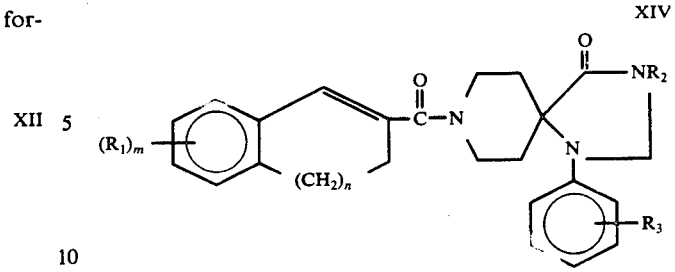

XIV by first reacting it with an organic base (e.g., triethylamine) and an alkyl haloformate to yield a mixed anhydride and then reacting the mixed anhydride with a compound of formula IV.

Reduction of an amide of formula XIV, preferably with sodium borohydride, yields a compound of formula Id. The reduction can be run in the presence of an organic base, e.g., pyridine.

An alternate, and preferred, procedure for obtaining compounds of formulas Ia, Ib, and Id wherein $R_1$ is hydroxy, is the hydrolysis of the corresponding alkanoyloxy derivative.

The starting ketones of formula II are known or can be synthesized by methods well known to those skilled in the art [cf. J. Amer. Chem. Soc., 89, 386 (1967); Can. J. Chem., 48, 1842 (1970); J. Chem. Soc. (c), 183 (1969); J. Med. Chem., 14, 90 (1971)].

The starting spiropiperidines of formula IV are known or can be synthesized by methods as described in U.S. Pat. 3,155,670 to Janssen.

The starting olefins of formula V are known or can be synthesized by several methods such as reacting the aryl-sulfonyl hydrazones of formula

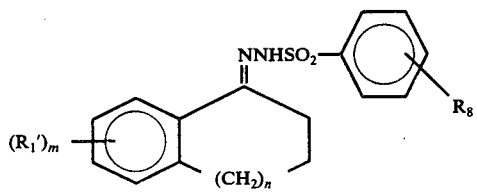

XV wherein $R_1'$ can be hydrogen, halogen, hydroxy, alkoxy, alkylthio, alkyl or trifluoromethyl and $R_8$ can be hydrogen or alkyl, with alkyllithium reagents having the formula

XVI $R_9$—LI wherein $R_9$ is an alkyl group having 1 to 8 carbon atoms. The reaction can be run in an organic solvent such as diethyl ether, tetrahydrofuran, decalin, hexane or benzene at a temperature of −70°, or just above the freezing point of the reaction mixture, to 100° C for 0.5 to 48 hours [cf. J. Am. Chem. Soc., 90, 4762 (1968) and references cited therein].

Other methods for the synthesis of olefins of formula V are also known [cf. Chem. Listy, 52, 353 (1958); J. Chem. Soc., 327 (1947); J. Am. Chem. Soc., 77, 601 (1955); Dokl. Akad. Nank. Belorussk, SSR, 5, 109 (1961); Ann. 576, 182 (1952); U.S. Pat. No. 3,393,247; U.S. Pat. No. 3,278,620; Ber., 96, 2730 (1963); Zhur. Obschei Khim, 27, 83 (1957); Ann. 540, 157 (1939); among others].

The hydrazones of formula XV are known and can be prepared by reacting ketones of the formula II with substituted hydrazines having the formula

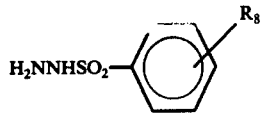

XVII according to standard procedures [cf. "The Systematic Identification of Organic Compounds", by R. L. Shriner, R. C. Fuson and D. Y. Curtin, 4th Ed., John Wiley & Sons, Inc., New York, 1959, p. 214ff and references cited therein].

The above described procedures yield the compounds of formulas I*a*, I*b*, I*c* and I*d* in the form of their free base or hydrohalide salt. The stable hydrohalide salt can be readily neutralized to yield the corresponding free base. The free base can, if desired, and if it is stable to the particular acid, be converted into other pharmaceutically acceptable acid-addition salts by reaction with either an inorganic or organic acid. Exemplary acids are sulfuric, nitric, phosphoric, boric, acetic, tartaric, maleic, citric, succinic, benzoic, ascorbic, salicyclic, methanesulfonic, benzenesulfonic, toluenesulfonic and the like.

The compounds of formula I*a* contain at least one assymmetric carbon atom (the carbon atom to which the [1-aryl-1,3,8-triazaspiro[4.5]decan-4-one]methyl group is attached). They exist as d,1 racemic mixtures.

The compounds of formula I*b* and I*c* contain at least two assymmetric carbon atoms (the carbon atom to which the hydroxyl or $R_4$ group is attached and the carbon atom to which the [1-aryl-1,3,8-triazaspiro[4.5]decan-4-one]methyl group is attached). They are capable of existing as at least four optically active forms or as at least two d,1 racemic mixtures, i.e., the d,1 forms of the trans and cis diastereomers.

The compounds of formulas I*b* and I*c* exist as mixtures of diastereomers and as racemic mixtures. They can be separated into cis and trans isomers by methods well known in the art; e.g., fractional crystallization and/or chromatography. Additionally, as is illustrated by the examples, controlling reaction conditions while reducing a Mannich base ketone of formula I*a* enables one to prepare either the cis or the trans diastereomer. Similarly, the racemic mixtures can be resolved into enantiomers using well known procedures; e.g., fractional crystallization of d- or l- tartrates, maleates, mandelates, N-acetylphenylalaninates, or camphor sulfonates, and reconverting the diastereomeric salts into the free enantiomers.

Compounds of formulas I*a*, I*b*, I*c* and I*d* wherein n is 1, and $R_1$ is hydrogen or 7-chloro are preferred.

Compounds of formulas I*a*, I*b*, I*c* and I*d* wherein $R_2$ is hydrogen are preferred.

Compounds of formula I wherein $R_3$ is hydrogen are preferred.

Furthermore, compounds wherein n is 1, m is 1, $R_1$ is alkyl or halogen and wherein $R_1$ is in the 6- or 7-position are preferred. In addition, when m is 2, it is preferred that $R_1$ is alkoxy or alkyl, the $R_1$ groups are in the 5- and 6-positions when n is 0 and in the 6- and 7-positions when n is 1, and n is 0 or 1.

The following examples are specific embodiments of this invention.

EXAMPLE 1

1-Phenyl-8-[(1,2,3,4-tetrahydro-1-oxo-2-naphthalenyl)-methyl]-1,3,8-triazaspiro[4.5]decan-4-one A. 2-[(Diethylamino)methyl]-3,4-dihydro-1(2H)-naphthalenone, hydrochloride (1:1)

α-Tetralone (292 g), diethylamine hydrochloride (240 g) and 37% aqueous formaldehyde (220 g) are combined and heated on a steam bath with stirring for 1 hour. The reaction mixture is cooled to 25° C and washed with three 120 ml portions of ether. The aqueous layer is made alkaline with concentrated ammonium chloride and extracted with chloroform. The chloroform is removed under vacuum and the residue taken up in ether. The resulting solution is treated with excess ethereal hydrogen chloride, producing an insoluble gum. The ether is decanted and the gum repeatedly scratched against the walls of the beaker to initiate a slow crystallization. The mass is allowed to stand overnight during which period crystallization is completed. The resulting solid mass is pulverized and washed with a minimal amount of ethanol. The mixture is filtered and the filter cake is stirred slowly in ether. The solid material is filtered off and dried for 4 hours at 25° C (0.1 mm of mercury) to yield 200 g of the title compound that melts beginning anywhere from 127° C to 135° C, depending on the rate of heating.

B. 1-Phenyl-8-[(1,2,3,4-tetrahydro-1-oxo-2-naphthalenyl)methyl]-1,3,8-triazaspiro[4.5]-decan-4-one 2-[(Diethylamino)methyl]-3,4-dihydro-1 (2H)-naphthalenone, hydrochloride (6.93 g) and 1-phenyl-1,3,8-triazaspiro-[4.5]decan-4-one (6.0 g.) are dissolved in 75 ml of methanol by brief heating, followed by stirring at room temperature for 16 hours. The resulting precipitate is filtered, washed with ethanol and dried at 80° C under vacuum to yield 8.58 g of the title compound, melting point 170°-173° C.

EXAMPLE 2

1-Phenyl-8-[(1,2,3,4-tetrahydro-1-oxo-2-naphthalenyl)-methyl]-1,3,8-triazaspiro-[4.5]decan-4-one, hydrochloride (1:1)

1-Phenyl-8-[(1,2,3,4-tetrahydro-1-oxo-2-naphthalenyl)methyl]-1,3,8-triazaspiro[4.5]decan-4-one (8.58 g) is digested with hot ethanol and dissolved in hot dioxane. The solution is filtered, cooled, and the salt precipitated by the addition of hydrochloric acid and ether. The salt is digested with hot ethanol and dried at 80° C under vacuum to yield 5.85 g of the title compound, melting point 190° C, which resolidifies to melt at 260°-261° C, dec.

EXAMPLE 3

1-Phenyl-8-[(trans-1,2,3,4-tetrahydro-1-hydroxy-2-naphthalenyl)methyl]-1,3,8-triazaspiro[4.5]decan-4-one 1-Phenyl-8-[(1,2,3,4-tetrahydro-1-oxo-2-naphthalenyl)methyl]-1,3,8-triazaspiro[4.5]decan-4-one (5.0 g) is suspended in methanol (100 ml) and treated over a 20 minute period with excess sodium borohydride dissolved in water (25 ml). The resulting mixture is stirred at room temperature for 15 hours. The reaction is diluted with water (200 ml), stirred for 30 minutes, and filtered to give the crude product. Two recrystallizations of this material from absolute ethanol yield 3.8 g of isomerically pure title compound, melting point 240°-242° C.

EXAMPLE 4

1-Phenyl-8-[(trans-1,2,3,4-tetrahydro-1-hydroxy-2-naphthalenyl)methyl]-1,3,8-triazaspiro[4.5]-decan-4-one, hydrochloride (1:1)

1-Phenyl-8-[(trans-1,2,3,4-tetrahydro-1-hydroxy-2-naphthalenyl)methyl]-1,3,8-triazaspiro[4.5]decan-4-one (3.7 g) is suspended in absolute ethanol (100 ml) and treated with 1.2 equivalents of ethereal hydrogen chloride. The resulting mixture is then digested on a steam bath for 10 minutes, cooled in an ice-bath, and filtered to yield 3.7 g of the title compound, melting point 248°–249° C.

EXAMPLE 5

1-Phenyl-8-[(cis-1,2,3,4-tetrahydro-1-hydroxy-2-naphthalenyl)methyl]-1,3,8-triazaspiro[4.5]decan-4-one 1-Phenyl-8-[(1,2,3,4-tetrahydro-1-oxo-2-naphthalenyl)methyl]-1,3,8-triazaspiro[4.5]decan-4-one (5.0 g) is dissolved in 60 ml of dry tetrahydrofuran and added, dropwise, to a flask charged with 2.1 equivalents of a 1 molar tetrahydrofuran solution of lithium tri-sec-butylborohydride, previously cooled to −78° C, all under an argon atmosphere. The resulting solution is stirred for 16 hours at room temperature. The reaction mixture is treated at 0° C with 15 ml of 3 molar sodium hydroxide followed by the addition of 15 ml of 30% hydrogen peroxide. The aqueous phase is saturated with potassium carbonate and the organic layer is separated and concentrated. The residue is dissolved in methylene chloride, washed with water, dried and concentrated producing the crude product. Recrystallization of this material from methylene chloride/hexane yields 4.2 g of isomerically pure title compound, melting point 204°–205° C.

EXAMPLE 6

1-Phenyl-8-[(cis-1,2,3,4-tetrahydro-1-hydroxy-2-naphthalenyl)methyl]-1,3,8-triazaspiro[4.5]decan-4-one, hydrochloride (1:1)

1-Phenyl-8-[(cis-1,2,3,4-tetrahydro-1-hydroxy-2-naphthalenyl)methyl]-1,3,8-triazaspiro[4.5]decan-4-one (4.0 g) is slurried in ether and treated with excess ethereal hydrogen chloride. The resulting mixture is cooled for 16 hours and the resulting precipitate is collected to yield 3.9 g of the title compound, melting point 254°–255° C.

EXAMPLE 7

1-Phenyl-8-[(1,2,3,4-tetrahydro-6-methoxy-1-oxo-2-naphthalenyl)methyl]-1,3,8-triazaspiro[4.5]-decan-4-one A solution of 2-[(dimethylamino)methyl]-3,4-dihydro-6-methoxy-1(2H)-naphthalenone (5.6 g, prepared as described in Jubilee Vol. Emil Barell, pg 264-305 (1946)) in 100 ml of warm absolute ethanol and a solution of 5.0 g of 1-phenyl-1,3,8-triazaspiro[4.5]decan-4-one in 75 ml of warm absolute ethanol are combined, refluxed for about 15 minutes, and allowed to stir at room temperature for 16 hours. The resulting precipitate is filtered to yield 6.4 g of material. Trituration with acetonitrile yields the title compound, melting point 177°–179° C.

EXAMPLE 8

1-Phenyl-8-[(1,2,3,4-tetrahydro-6-methoxy-1-oxo-2-naphthalenyl)methyl]-1,3,8-triazaspiro-[4.5]decan-4-one, hydrochloride (1:1)

1-Phenyl-8-[(1,2,3,4-tetrahydro-6-methoxy-1-oxo-2-naphthalenyl)methyl]-1,3,8-triazaspiro[4.5]decan-4-one (6.0 g) is finely ground and slurried in absolute ethanol (200 ml). While cooling the mixture at 0° C, ethanolic hydrogen chloride solution (1 equivalent) is added dropwise. The resulting mixture is stirred at room temperature for 15 minutes, heated on a steam bath for 10 minutes and allowed to stand at room temperature for 2 hours. The solid product is collected, washed with absolute ethanol, and dried under vacuum to yield 5.2 g of the title compound, melting point 203°–204° C.

EXAMPLE 9

1-Phenyl-8-[(trans-1,2,3,4-tetahydro-1-hydroxy-6-methoxy-2-naphthalenyl)methyl]-1,3,8-triazaspiro[4.5]decan-4-one 1-Phenyl-8-[(1,2,3,4-tetrahydro-6-methoxy-1-oxo-2-naphthalenyl)methyl]-1,3,8-triazaspiro[4.5]decan-4-one (4.0 g) is slurried in 150 ml of methanol and treated dropwise with excess sodium borohydride dissolved in 15 ml of water. The resulting mixture is stirred at room temperature for 16 hours. The solids are collected and washed with additional methanol yielding the crude product. Two crystallizations of this material from absolute ethanol give 3.0 g of isomerically pure title compound, melting point 219°–220° C.

EXAMPLE 10

1-Phenyl-8-[(trans-1,2,3,4-tetrahydro-1-hydroxy-6-methoxy-2-naphthalenyl)methyl]-1,3,8-triazaspiro-[4.5]decan-4-one, hydrochloride (1:1)

1-Phenyl-8-[(trans-1,2,3,4-tetrahydro-1-hydroxy-6-methoxy-2-naphthalenyl)methyl]-1,3,8-triazaspiro[4.5]-decan-4-one (2.5 g) is suspended in 100 ml of anhydrous ether and treated with one equivalent of ethereal hydrogen chloride. The resulting mixture is stirred at room temperature for one hour and then cooled. The precipitate is collected and washed with additional ether to yield 2.4 g of the title compound, melting point 258°–260° C.

EXAMPLE 11

1-Phenyl-8-[(cis-1,2,3,4-tetrahydro-1-hydroxy-6-methoxy-2-naphthalenyl)methyl]-1,3,8-triazaspiro[4.5]-decan-4-one 1-Phenyl-8-[(1,2,3,4-tetrahydro-6-methoxy-1-oxo-2-naphthalenyl)methyl]-1,3,8-triazaspiro[4.5]decan-4-one (5.4 g) dissolved in 60 ml of dry tetrahydrofuran is added dropwise to a flask charged with 2.1 equivalents of a 1 molar tetrahydrofuran solution of lithium tri-sec-butylborohydride which has been cooled to −78° C under an argon atmosphere. The resulting solution is stirred for 16 hours at room temperature. The reaction mixture is treated at 0° C with 15 ml of 3 molar sodium hydroxide followed by the addition of 15 ml of 30% hydrogen peroxide. The aqueous phase is saturated with potassium carbonate and the organic layer is separated and concentrated. The residue is dissolved in methylene chloride, washed with water, dried and concentrated producing the crude product. Two crystallizations of this material from absolute ethanol/methylene chloride yield 3.8 g of isomerically pure title compound, melting point 182°–183° C.

EXAMPLE 12

1-Phenyl-8-[(cis-1,2,3,4-tetrahydro-1-hydroxy-6-methoxy-2-naphthalenyl)methyl]-1,3,8-triazaspiro[4.5]decan-4-one, hydrochloride (1:1)

1-Phenyl-8-[(cis-1,2,3,4-tetrahydro-1-hydroxy-6-methoxy-2-naphthalenyl)methyl]-1,3,8-triazaspiro[4.5]decan-4-one (2.5 g) is suspended in 100 ml of anhydrous ether and treated with one equivalent of etheral hydrogen chloride. The resulting mixture is stirred at room temperature for one hour and then cooled. The precipitate is collected and washed with additional ether to yield 2.1 g of the title compound, melting point 243°–244° C.

EXAMPLE 13

8-[(2,3-Dihydro-5,6-dimethoxy-1-oxo-1H-inden-2-yl)methyl]-1-phenyl-1,3,8-triazaspiro[4.5]-decan-4-one A. 2-[(Dimethylamino)methyl]-5,6-dimethoxy-1-indanone, hydrochloride (1:1)

5,6-Dimethoxy-1-indanone (5.0 g), paraformaldehyde (1.6 g) and dimethylamine hydrochloride (2.7 g) are suspended in 15 ml of absolute ethanol, treated with 0.43 ml of concentrated hydrochloric acid and the mixture refluxed for 7 hours. The resulting suspension is cooled, diluted with 100 ml of acetone, stirred for 10 to 15 minutes and the precipitate filtered off to yield 4.0 g of the title compound, melting point 178°–180° C.

B. 8-[(2,3-Dihydro-5,6-dimethoxy-1-oxo-1H-inden-2-yl)methyl]-1-phenyl-1,3,8-triazaspiro[4.5]decan-4-one 2-[(Dimethylamino)methyl]-5,6-dimethoxy-1-indanone, hydrochloride (1:1) (2.0 g) and 1-phenyl-1,3,8-triazaspiro[4.5]decan-4-one (1.94 g) are stirred for 20 hours in 20 ml of absolute ethanol while a slow stream of nitrogen is bubbled through. The resultant precipitate is filtered off and dried to yield 2.75 g of the title compound, melting point 174°–177° C.

EXAMPLE 14

8-[(2,3-Dihydro-5,6-dimethoxy-1-oxo-1H-inden-2-yl)methyl]-1-phenyl-1,3,8-triazaspiro[4.5]-decan-4-one, hydrochloride (1:1)

8-[(2,3-Dihydro-5,6-dimethoxy-1-oxo-1H-inden-2-yl)methyl]-1-phenyl-1,3,8-triazaspiro[4.5]decan-4-one (2.75 g) is taken up in 400 ml of boiling dioxane and filtered while hot. The filtrate is concentrated to half its original volume, cooled and treated with 1.2 equivalents of a solution of hydrogen chloride in dioxane. The resulting solution is then diluted with 200 ml of ether and chilled. The crude hydrochloride salt thus obtained is triturated with boiling absolute ethanol (50 ml), cooled and filtered to yield 1.68 g of the title compound, melting point 210°–211° C.

EXAMPLE 15 trans-8-[(2,3-Dihydro-1-hydroxy-5,6-dimethoxy-1H-inden-2-yl)methyl]-1-phenyl-1,3,8-triazaspiro[4.5]decan-4-one 8-[(2,3-Dihydro-5,6-dimethoxy-1-oxo-1H-inden-2-yl)methyl]-1-phenyl-1,3,8-triazaspiro[4.5]decan-4-one, hydrochloride (1:1) (20.0 g finely ground) is slurried in methanol (400 ml), cooled in ice, and treated dropwise with an excess of sodium borohydride dissolved in water (75 ml). The resulting mixture is stirred for 16 hours at room temperature. Dilution with water (400 ml), extraction with methylene chloride, and concentration of the dried methylene chloride extracts in vacuo yield the crude product. Crystallization of this material from absolute ethanol yields 13.3 g of isomerically pure title compound, melting point 189°–190° C.

EXAMPLE 16

1-Phenyl-8-[(cis-1,2,3,4-tetrahydro-1-hydroxy-6-methoxy-2-naphthalenyl)methyl]-1,3,8-triazaspiro[4.5]decan-4-one and
1-Phenyl-8-[(trans-1,2,3,4-tetrahydro-1-hydroxy-6-methoxy-2-naphthalenyl)methyl]-1,3,8-triazaspiro[4.5]decan-4-one 1-Phenyl-8-[(1,2,3,4-tetrahydro-6-methoxy-1-oxo-2-naphthalenyl)methyl]-1,3,8-triazaspiro[4.5]decan-4-one (5.0 g) is hydrogenated at room temperature at atmospheric pressure in 200 ml of dioxane containing platinum oxide (1.0 g). A catalytic amount of ferric chloride is added to the reaction mixture. After the theoretical amount of hydrogen is taken up, the reaction mixture is filtered and concentrated to yield a 2:1 trans/cis mixture of the title compounds.

This mixture is fractionally recrystallized several times from absolute ethanol whereby 2.7 g of the less soluble trans — title compound is obtained as a precipitate, melting 219°–220° C.

The filtrates remaining after the isolation of the trans isomer are combined and successively concentrated and filtered to remove residual trans isomer. The mother liquor is concentrated to a minimum volume to give 1.1 g of the crude cis — title compound, melting point 174°–178° C.

EXAMPLES 17–47

Following the procedure of Example 1, but substituting the compound listed in column I for α-tetralone and the compound listed in column II for 1-phenyl-1,3,8-triazaspiro[4.5]decan-4-one, the compound listed in column III is obtained. In those examples utilizing a benzosuberone starting material the Mannich reaction is run in an oil bath maintained at 120° C, rather than in a steam bath.

| Example | Column I | Column II | Column III |
| --- | --- | --- | --- |
| 17 | 6-chloro-α-tetralone | 3-methyl-1-phenyl-1,3,8-triazaspiro[4.5]decan-4-one | 3-methyl-1-phenyl-8-[(1,2,3,4-tetrahydro-6-chloro-1-oxo-2-naphthalenyl)methyl]-1,3,8-triazaspiro[4.5]decan-4-one |
| 18 | 6-(trifluoromethyl)-α-tetralone | 1-phenyl-3-(2-propenyl)-1,3,8-triazaspiro[4.5]-decan-4-one | 1-phenyl-3-(2-propenyl)-8-[(1,2,3,4-tetrahydro-6-(trifluoromethyl)-1-oxo-2-naphthalenyl)methyl]-1,3,8-triazaspiro[4.5]decan-4-one |
| 19 | 6-acetoxy-α-tetralone | 1-phenyl-1,3,8-triazaspiro[4.5]decan-4-one | 1-phenyl-8-[1,2,3,4-tetrahydro-6-acetoxy-1-oxo-2-naphthalenyl)- |

-continued

| Example | Column I | Column II | Column III |
|---|---|---|---|
| | | | methyl]-1,3,8-triazaspiro[4.5]-decan-4-one |
| 20 | 6-methylthio-α-tetralone | 1-phenyl-1,3,8-triazaspiro[4.5]decan-4-one | 1-phenyl-8-[(1,2,3,4-tetrahydro-6-methylthio-1-oxo-2-naphthalenyl)methyl]-1,3,8-triazaspiro-[4.5]decan-4-one |
| 21 | 6-methyl-α-tetralone | 1-phenyl-1,3,8-triazaspiro[4.5]decan-4-one | 1-phenyl-8-[1,2,3,4-tetrahydro-6-metyl-1-oxo-2-naphthalenyl)-methyl]-1,3,8-triazaspiro[4.5]-decan-4-one |
| 22 | 6-ethyl-α-tetralone | 1-(4-chlorophenyl)-1,3,8-triazaspiro[4.5]-decan-4-one | 1-(4-chlorophenyl)-8-[(1,2,3,4-tetrahydro-6-ethyl-1-oxo-2-naphthalenyl)methyl]-1,3,8-triazaspiro[4.5]decan-4-one |
| 23 | 6,7-dimethoxy-α-tetralone | 1-(4-fluorophenyl)-1,3,8-triazaspiro[4.5]decan-4-one | 1-(4-fluorophenyl)-8-[(1,2,3,4-tetrahydro-6,7-dimethoxy-1-oxo-2-naphthalenyl)methyl]-1,3,8-triazaspiro[4.5]decan-4-one |
| 24 | 6,7-dimethyl-α-tetralone | 1-(4-methylphenyl)-1,3,8-triazaspiro[4.5]decan-4-one | 1-(4-methylphenyl)-8-[(1,2,3,4-tetrahydro-6,7-dimethyl-1-oxo-2-naphthalenyl)methyl]-1,3,8-triazaspiro[4.5]decan-4-one |
| 25 | 5-fluoro-1-indanone | 1-phenyl-1,3,8-triazaspiro[4.5]decan-4-one | 8-[(2,3-dihydro-5-fluoro-1-oxo-1H-inden-2-yl)methyl]-1-phenyl-1,3,8-triazaspiro[4.5]decan-4-one |
| 26 | 5-chloro-1-indanone | 1-phenyl-1,3,8-triazaspiro[4.5]decan-4-one | 8-[(2,3-dihydro-5-chloro-1-oxo-1H-iden-2-yl)methyl]-1-phenyl-1,3,8-triazaspiro[4.5]decan-4-one |
| 27 | 5-acetoxy-1-indanone | 1-phenyl-1,3,8-triazaspiro[4.5]decan-4-one | 8-[(2,3-dihydro-5-acetoxy-1-oxo-1H-inden-2-yl)methyl]-1-phenyl-1,3,8-triazaspiro[4.5]decan-4-one |
| 28 | 5-ethylthio-1-indanone | 1-phenyl-1,3,8-triazaspiro[4.5]decan-4-one | 8-[(2,3-dihydro-5-ethylthio-1-oxo-1H-inden-2-yl)methyl]-1-phenyl-1,3,8-triazaspiro[4.5]decan-4-one |
| 29 | 5-ethyl-1-indanone | 1-phenyl-1,3,8-triazaspiro[4.5]decan-4-one | 8-[(2,3-dihydro-5-ethyl-1-oxo-1H-inden-2-yl)methyl]-1-phenyl-1,3,8-triazaspiro[4.5]decan-4-one |
| 30 | 5-(trifluoromethyl)-1-indanone | 1-phenyl-1,3,8-triazaspiro[4.5]decan-4-one | 8-[(2,3-dihydro-5-(trifluoromethyl)-1-oxo-1H-inden-2-yl)methyl]-1-phenyl-1,3,8-triazaspiro[4.5]-decan-4-one |
| 31 | 1-indanone | 3-ethyl-1-phenyl-1,3,8-triazaspiro[4.5]decan-4-one | 8-[(2,3-dihydro-1-oxo-1H-inden-2-yl)methyl]-3-ethyl-1-phenyl-1,3,8-triazaspiro[4.5]decan-4-one |
| 32 | 1-indanone | 3-propyl-1-phenyl-1,3,8-triazaspiro[4.5]decan-4-one | 8-[(2,3-dihydro-1-oxo-1H-inden-2-yl)methyl]-3-propyl-1-phenyl-1,3,8-triazaspiro[4.5]decan-4-one |
| 33 | 1-indanone | 1-(4-chlorophenyl)-1,3,8-triazaspiro[4.5]decan-4-one | 8-[(2,3-dihydro-1-oxo-1H-inden-2-yl)methyl]-1-(4-chlorophenyl)-1,3,8-triazasiro[4.5]decan-4-one |
| 34 | 1-indanone | 1-(4-ethylphenyl)-1,3,8-triazaspiro[4.5]9 decan-4-one | 8-[2,3-dihydro-1-oxo-1H-inden-2-yl)-methyl]-1-(4-ethylphenyl)-1,3,8-triazaspiro[4.5]decan-4-one |
| 35 | 1-benzosuberone | 1-phenyl-1,3,8-triazaspiro[4.5]decan-4-one | 1-phenyl-8-[(6,7,8,9-tetrahydro-5-oxo-benzocyclohepten-6-yl)methyl]-1,3,8-triazaspiro[4.5]decan-4-one |
| 36 | 7-chloro-1-benzosuberone | 1-phenyl-1,3,8-triazaspiro[4.5]decan-4-one | 1-phenyl8-[6,7,8,9-tetrahydro-2-chloro-5-oxo-benzocyclohepten-6-yl)methyl]-1,3,8-triazaspiro[4.5]decan-4-one |
| 37 | 7-bromo-1-benzosuberone | 1-phenyl-1,3,8-triazaspiro[4.5]decan-4-one | 1-phenyl-8-[(6,7,8,9-tetrahydro-2-bromo-5-oxo-benzocyclohepten-S 6-yl)methyl]-1,3,8-triazaspiro-[4.5]decan-4-one |
| 38 | 7-fluoro-1-benzosuberone | 1-phenyl-1,3,8-triazaspiro[4.5]decan-4-one | 1-phenyl-8-[(6,7,8,9-tetrahydro-2-fluoro-5-oxo-benzocyclohepten-6-yl)methyl]-1,3,8-triazaspiro-[4.5]decan-4-one |
| 39 | 7-acetoxy-1-benzosuberone | 1-phenyl-1,3,8-triazaspiro[4.5]decan-4-one | 1-phenyl-8-[6,7,8,9-tetrahydro-2-acetoxy-5-oxo-benzocyclohepten-6-yl)methyl]-1,3,8-triazaspiro-[4.5]decan-4-one |
| 40 | 7-methoxy-1-benzosuberone | 1-phenyl-1,3,8-triazaspiro[4.5]decan-4-one | 1-phenyl-8-[(6,7,8,9-tetrahydro-2-methoxy-5-oxo-benzocyclohepten-6-yl)methyl]-1,3,8-triazaspiro-[4.5]decan-4-one |
| 41 | 7-(trifluoromethyl)-1-benzosuberone | 1-phenyl-1,3,8-triazaspiro[4.5]decan-4-one | 1-phenyl-8-[(6,7,8-tetrahydro-2-(trifluoromethyl)-5-oxo-benzocyclohepten-6-yl)metyl]-1,3,8-triazaspiro[4.5]decan-4-one |
| 42 | 7,8-dimethoxy-1-benzosuberone | 1-phenyl-1,3,8-triazaspiro[4.5]decan-4-one | 1-phenyl-8-[(6,7,8,9-tetrahydro-2,3-dimethoxy-5-oxo-benzocyclohepten-6-yl)methyl]-1,3,8-triazaspiro[4.5]decan-4-one |
| 43 | 7,8-dimethyl-1-benzosuberone | 1-phenyl-1,3,8-triazaspiro[4.5]decan-4-one | 1-phenyl-8-[(6,7,8,9-tetrahydro-2,3-dimethyl-5-oxo-benzocyclohepten-6-yl)methyl]-1,3,8-triazasiro[4.5]decan-4-one |
| 44 | 1-benzosuberone | 1-(4-chlorophenyl)-1,3,8-triazaspiro[4.5]decan-4-one | 1-(4-chlorophenyl)-8-[(6,7,8,9-tetrahydro-5-oxo-benzocyclohepten-6-yl)methyl]-1,3,8-triazaspiro[4.5]decan-4-one |

-continued

| Example | Column I | Column II | Column III |
|---|---|---|---|
| 45 | 1-benzosuberone | 1-(4-methylphenyl9-1,3,8-triazaspiro-[4.5]decan-4-one | 1-(4-methylphenyl)-8-[(6,7,8,9-tetrahydro-5-oxo-benzocyclohepten-6-yl)methyl]-1,3,8-triazaspiro-[4.5]decan-4-one |
| 46 | 1-benzosuberone | 3-(2-butenyl)-1-phenyl-1,3,8-triazaspiro[4.5]-1,3,8-triazaspiro[4.5]-decan-4-one | 3-(2-butenyl)-1-phenyl-8-[(6,7,8,9-tetrahydro-5-oxo-benzocyclohepten-tetrahydro-5-oxo-benzocyclohepten-6-yl)methyl]-1,3,8-triazaspiro-[4.5]decan-4-one |
| 47 | 1-benzosuberone | 3-methyl-1-phenyl-1,3,8-triazaspiro[4.5]decan-4-one | 3-methyl-1-phenyl-8-[(6,7,8,9-tetrahydro-5-oxo-benzocyclohepten-6-yl)methyl]-1,3,8-triazaspiro-[4.5]decan-4-one |

EXAMPLES 48–50

The compound listed in column I (0.01 mole) is added to 30 ml of 8% methanolic potassium hydroxide, refluxed for 3 minutes under argon, cooled to room temperature and diluted with sufficient water to effect solution. Excess aqueous ammonium chloride solution is added dropwise, with stirring, and the reaction mixture is extracted several times with methylene chloride. The organic extracts are dried, filtered and evaporated to give the compound listed in column II.

| Example | Column I | Column II |
|---|---|---|
| 48 | 1-phenyl-8-[(1,2,3,4-tetrahydro-6-acetoxy-1-oxo-2-naphthalenyl)methyl]-1,3,8-triazaspiro[4.5]decan-4-one | 1-phenyl-8-[(1,2,3,4-tetrahydro-6-hydroxy-1-oxo-2-naphthalenyl)methyl]-1,3,8-triazaspiro[4.5]decan-4-one |
| 49 | 8-[(2,3-dihydro-5-acetoxy-1-oxo-1H-inden-2-yl)methyl]-1-phenyl-1,3,8-triazaspiro[4.5]decan-4-one | 8-[(2,3-dihyro-5-hydroxy-1-oxo-1H-inden-2-yl)methyl]-1-phenyl-1,3,8-triazaspiro-[4.5]decan-4-one |
| 50 | 1-phenyl-8-[(6,7,8,9-tetrahydro-2-acetoxy-5-oxo-benzocyclohepten-6-yl)methyl]-1,3,8-triazaspiro[4.5]-decan-4-one | 1-phenyl-8-[(6,7,8,9-tetrahydro-2-hydroxy-5-oxo-benzocyclohepten-6-yl)methyl]-1,3,8-triazaspiro[4.5]decan-4-one |

EXAMPLES 51–81

Following the procedure of Example 16, but not separating the diastereomers, and substituting the compound listed in column I for 1-phenyl-8-[(1,2,3,4-tetrahydro-6-methoxy-1-oxo-2-naphthalenyl)methyl]-1,3,8-triazaspiro[4.5]decan-4-one, the compound listed in column II is obtained.

| Example | Column I | Column II |
|---|---|---|
| 51 | 3-methyl-1-phenyl-8-[(1,2,3,4-tetrahydro-6-chloro-1-oxo-2-naphthalenyl)methyl]-1,3,8-triazaspiro[4.5]decan-4-one | 3-methyl-1-phenyl-8-[(1,2,3,4-tetrahydro-6-chloro-1-hydroxy-2-naphthalenyl)methyl]-1,3,8-triazaspiro[4.5]decan-4-one |
| 52 | 1-phenyl-3-(2-propenyl)-8-[(1,2,3,4-tetrahydro-6-(trifluoromethyl)-1-oxo-2-naphthalenyl)methyl]-1,3,8-triazaspiro[4.5]decan-4-one | 1-phenyl-3-(2-propenyl)-8-[(1,2,3,4-tetrahydro-6-(trifluoromethyl)-1-hydroxy-2-naphthalenyl)methyl]-1,3,8-triazaspiro[4.5]decan-4-one |
| 53 | 1-phenyl-8-[(1,2,3,4-tetrahydro-6-methylthio-1-oxo-2-naphthalenyl)methyl]-1,3,8-triazaspiro[4.5]decan-4-one | 1-phenyl-8-[(1,2,3,4-tetrahydro-6-methylthio-1-hydroxy-2-naphthalenyl)methyl]-1,3,8-triazaspiro[4.5]decan-4-one |
| 54 | 1-phenyl-8-[(1,2,3,4-tetrahydro-6-methyl-1-oxo-2-naphthalenyl)methyl]-1,3,8-triazaspiro[4.5]decan-4-one | 1-phenyl-8-[(1,2,3,4-tetrahydro-6-methyl-1-hydroxy-2-naphthalenyl)methyl]-1,3,8-triazasiro[4.5]decan-4-one |
| 55 | 1-(4-chlorophenyl)-8-[(1,2,3,4-tetrahydro-6-ethyl-1-oxo-2-naphthalenyl)methyl]-1,3,8-triazaspiro[4.5]decan-4-one | 1-(4-chlorophenyl)-8-[(1,2,3,4-tetrahydro-6-ethyl-1-hydroxy-2-naphthalenyl)methyl]-1,3,8-triazaspiro[4.5]decan-4-one |
| 56 | 1-(4-fluorophenyl)-8-[(1,2,3,4-tetrahydro-6,7-dimethoxy-1-oxo-2-naphthalenyl)methyl]-1,3,8-triazaspiro[4.5]decan-4-one | 1-(4-fluorophenyl)-8-[(1,2,3,4-tetrahydro-6,7-dimethoxy-1-hydroxy-2-naphthalenyl)methyl]-1,3,8-triazaspiro[4.5]decan-4-one |
| 57 | 1-(4-methylphenyl)-8-[(1,2,3,4-tetrahydro-6,7-dimethyl-1-oxo-2-naphthalenyl)methyl]-1,3,8-triazaspiro[4.5]decan-4-one | 1-(4-methylphenyl)-8-[(1,2,3,4-tetrahydro-S 6,7-dimethyl-1-hydroxy-2-naphthalenyl)-methyl]-1,3,8-triazaspiro[4.5]decan-4-one |
| 58 | 8-[(2,3-dihydro-5-fluoro-1-oxo-1H-inden-2-yl)methyl]-1-phenyl-1,3,8-triazaspiro-[4.5]decan-4-one | 8-[(2,3-dihyro-5-fluoro-1-hydroxy-1H-inden-2-yl)methyl]-1-phenyl-1,3,8-triazaspiro[4.5]decan-4-one |
| 59 | 8-[(2,3-dihydro-5-chloro-1-oxo-1-H-inden-2-yl)methyl]-1-phenyl-1,3,8-triazaspiro-[4.5]-decan-4-one | 8-((2,3-:dihydro-5-chloro-1-hydroxy-1H-inden-2-yl)methyl]-1-phenyl-1,3,8-triazaspiro[4.5]decan-4-one |
| 60 | 8-[(2,3-dihydro-5-ethylthio-1-oxo-1H-inden-2-yl)methyl]-1-phenyl-1,3,8-triazaspiro-[4.5]decan-4-one | 8-[(2,3-dihydro-5-ethylthio-1-hydroxy-1H-inden-2-yl)methyl]-1-phenyl-1,3,8-triazaspiro[4.5]decan-4-one |
| 61 | 8-[(2,3-dihydro-5-ethyl-1-oxo-1H-inden-2-yl)methyl]-1-phenyl-1,3,8-triazaspiro-[4.5]decan-4-one | 8-[(2,3-dihydro-5-ethyl-1-hydroxy-1H-inden-2-yl)methyl]-1-phenyl-1,3,8-triazaspiro[4.5]decan-4-one |
| 61 | 8-[2,3-dihydro-5-(trifluoromethyl)-1-oxo-1H-inden-2-yl)methyl]-1-phenyl-1,3,8-triazaspiro[4.5]decan-4-one | 8-[(2,3-dihydro-5-(trifluoromethyl)-1-hydroxy-1H-inden-2-yl)methyl]-1-phenyl-1,3,8-triazaspiro(4.5]decan-4-one |
| 63 | 8-[(2,3-dihydro-1-oxo-1H-inden-2-yl)-methyl]-3-ethyl-1-phenyl-1,3,8-triazaspiro[4.5]decan-4-one | 8-[(2,3-dihydro-1-hydroxy-1H-inden-2-yl)-methyl]-3-ethyl-1-phenyl-1,3,8-triazaspiro[4.5]decan-4-one |
| 64 | 8-[(2,3-dihydro-1-oxo-1H-inden-2-yl)-methyl]-3-propyl-1-phenyl-1,3,8-triazaspiro[4.5]decan-4-one | 8-[(2,3-dihydro-1-hydroxy-1H-inden-2-yl)-methyl]-3-propyl-1-phenyl-1,3,8-triazaspiro[4.5]decan-4-one |

-continued

| Example | Column I | Column II |
|---|---|---|
| 65 | 8-[(2,3-dihydro-1-oxo-1-H-inden-2-yl)-methyl]-1-(4-chlorophenyl)-1,3,8-triazaspiro[4.5]decan-4-one | 8-[(2,3-dihydro-1-hydroxy-1H-inden-2-yl)-methyl]-1-(4-chlorophenyl)-1,3,8-triazaspiro[4.5]decan-4-one |
| 66 | 8-[(2,3-dihydro-1-oxo-1H-inden-2-yl)-methyl]-1-(4-ethylphenyl)-1,3,8-trimethyl]-1-(4-ethylphenyl)-1,3,8-triazaazaspiro[4.5]decan-4-one | 8-[(2,3-dihydro-1-hyroxy-1H-inden-2-yl)-spiro[4.5]decan-4-one |
| 67 | 1-phenyl-8-[(6,7,8,9-tetrahydro-5-oxo-benzocyclohepten-6-yl)methyl]-1,3,8-triazaspiro[4.5]decan-4-one | 1-phenyl-8-[(6,7,8,9-tetrahydro-5-hydroxy-benzocyclohepten6-yl)methyl]-1,3,8-triazaspiro[4.5]decan-4-one |
| 68 | 1-phenyl-8-[(6,7,8,9-tetrahydro-2-chloro-5-oxo-benzocyclohepten-6-yl)-methyl]-1,3,8-triazaspiro[4.5]decan-4-one | 1-phenyl-8-[(6,7,8,9-tetrahydro-2-chloro-5-hydroxy-benzocyclohepten-6-yl)methyl]-1,3,8-triazaspiro[4.5]decan-4-one |
| 69 | 1-phenyl-8-[(6,7,8,9-tetrahydro-7-bromo-5-oxo-benzocyclohepten-6-yl)-methyl]-1,3,8-triazaspiro[4.5]decan-4-one | 1-phenyl-8-[(6,7,8,9-tetrahydro-7-bromo-5-hydroxy-benzocyclohepten-6-yl)methyl]-1,3,8-triazaspiro[4.5]decan-4-one |
| 70 | 1phenyl-8-[(6,7,8,9-tetrahydro-2-fluoro-5-oxo-benzocyclohepten-6-yl)methyl]-1,3,8-triazaspiro[4.5]decan-4-one | 1phenyl-8-[86,7,8,9-tetrahydro-2-fluoro-5-hydroxy-benzocyclohepten-6-yl)metnhyl]-1,3,8-triazaspiro[4.5]decan-4-one |
| 71 | 1-phenyl-8-[(6,7,8,9-tetrahydro-2-methoxy-5-oxo-benzocyclohepten-6-yl)-methyl]-1,3,8-triazaspiro[4.5]decan-4-one | 1-phenyl-8-[(6,7,8,9-tetrahydro-2-methoxy-5-hydroxy-benzocyclohepten-6-yl)methyl]-1,3,8-triazaspiro[4.5]decan-4-one |
| 72 | 1-phenyl-8-[(6,7,8,9-tetrahydro-2-(trifluoromethyl)-5-oxo-benzocyclohepten-6-yl)methyl]-1,3,8-triazaspiro[4.5]decan-4-one | 1-phenyl-8-[(6,7,8,9-tetrahydro-2-(trifluoromethyl)-5-hydroxy-benzocyclohepten-6-yl)methyl]-1,3,8-triazaspiro( 4.5]decan-4-one |
| 73 | 1-phenyl-8-[(6,7,8,9-tetrahydro-2,3-dimethoxy-5-oxo-benzocyclohepten-6-yl)methyl]-1,3,8-triazaspiro[4.5]decan-4-one | 1-phenyl-8-[(6,7,8,9-tetrahydro-2,3-dimethoxy-5-hydroxy-benzocyclohepten-6-yl)-methyl]-1,3,8-triazaspiro( 4.5]decan-4-one |
| 74 | 1-phenyl-8-[(6,7,8,9-tetrahydro-2,3-dimethyl-5-oxo-benzocyclohepten-6-yl)methyl]-1,3,8-triazaspiro[4.5]decan-4-one | 1-phenyl-8-[(6,7,8,9-tetrahydro-2,3-dimethyl-5-hydroxy-benzocyclohepten-6-yl)-methyl]-1,3,8-triazaspiro[4.5]decan-4-one |
| 75 | 1-(4-chlorophenyl)-8-[(6,7,8,9-tetrahydro-5-oxo-benzocyclohepten-6-yl)-methyl]-1,3,8-triazaspiro( 4.5]decan-4-one | 1-(4-chlorophenyl)-8-[(6,7,8,9-tetrahydro-5-hydroxy-benzocyclohepten-6-yl)methyl]-1,3,8-triazaspiro[4.5]decan-4-one |
| 76 | 1-(4-methylphenyl)-8-[(6,7,8,9-tetrahydro-5-oxo-benzocyclohepten-6-yl)-methyl]-1,3,8-triazaspiro[4.5]decan-4-one | 1-(4-methylphenyl)-8-[(6,7,8,9-tetrahydro-5-hydroxy-benzocyclohepten-6-yl)methyl]-1,3,8-triazaspiro[4.5]decan-4-one |
| 77 | 3-(2-butenyl)-1-phenyl-8-[(6,7,8,9-tetrahydro-5-oxo-benzocyclohepten-6-yl)methyl]-1,3,8-triazaspiro[4.5]decan-4-one | 3-(2-butenyl)-1-phenyl-8-[(6,7,8,9-tetrahydro-5-hydroxy-benzocyclohepten-6-yl)-methyl]-1,3,8-triazaspiro[4.5]decan-4-one |
| 78 | 3-methyl-1-phenyl-8-[(6,7,8,9-tetrahydro-5-oxo-benzocyclohepten-6-yl)methyl]-1,3,8-triazaspiro[4.5]decan-4-one | 3-methyl-1-phenyl-8-[(6,7,8,9-tetrahydro-5-hydroxy-benzocyclohepten-6-yl)methyl]-1,3,8-triazaspiro[4.5]decan-4-one |
| 79 | 1-phenyl-8-[(1,2,3,4-tetrahydro-6-acetoxy-1-oxo-2-naphthalenyl)methyl]-1,3,8-triazaspiro[4.5]decan-4-one | 1-phenyl-8-[(1,2,3,4-tetrahydro-6-acetoxy-1-hydroxy-2-naphthalenyl)methyl]1,3,8-triazaspiro[4.5]decan-4-one |
| 80 | 8-[(2,3-dihydro-5-acetoxy-1-oxo-1H-inden-2-yl)methyl]-1-phenyl-1,3,8-triazaspiro[4.5]decan-4-one | 8-[(2,3-dihydro-5-acetoxy-1-hydroxy-1H-inden-2-yl)methyl]-1-phenyl-1,3,8-triazaspiro[4.5]decan-4-one |
| 81 | 1-phenyl-8-[(6,7,8,9-tetrahydro-2-acetoxy-5-oxo-benzocyclohepten-6-yl)methyl]-1,3,8-trazaspiro[4.5]decan-4-one | 1-phenyl-8-[(6,7,8,9-tetrahydro-2-acetoxy-5-hydroxy-benzocyclohepten-6-yl)methyl]-1,3,8-triazaspiro[4.5]decan-4-one |

EXAMPLE 82 trans-8-[[2,3-Dihydro-1-(formyloxy)-5,6-dimethoxy-1H-inden-2-yl]methyl]-1-phenyl-1,3,8-triazaspiro[4.5]decan-4-one To 0.11 mole of a stirred formic acid-acetic anhydride mixture (prepared as described in Rec. Trav. Chem., 83, 1287 (1964) is added 0.10 mole of trans-8-[(2,3-dihydro-1-hydroxy-5,6-dimethoxy-1H-inden-2-yl)methyl]-1-phenyl-1,3,8-triazaspiro[4.5]decan-4-one. The temperature of the reaction mixture is maintained below 20° C and stirring is continued for 12 days under argon. The reaction mixture is then poured, with stirring, into excess ice-cold aqueous sodium bicarbonate, extracted with ether and the ether extracts dried with anhydrous sodium sulfate. The ether is evaporated and the residue is crystallized from cyclohexane to give the title compound.

EXAMPLE 83

8-[[trans-1-(Acetyloxy)-1,2,3,4-tetrahydro-2-naphthalenyl]methyl]-1-phenyl-1,3,8-triazaspiro[4.5]decan-4-one, maleate salt (1:1)

1-Phenyl-8-[(trans-1,2,3,4-tetrahydro-1-hydroxy-2-naphthalenyl)methyl]-1,3,8-triazaspiro[4.5]decan-4-one (3.0 g) is dissolved in 30 ml of anhydrous pyridine and treated with 15 ml of acetic anhydride. The mixture is stirred at room temperature for 6 hours and then poured into 400 ml of ice-water and stirred for 1 hour. The resulting aqueous suspension is extracted with methylene chloride and washed with saturated sodium bicarbonate solution, dried, and concentrated yielding the crude acetate. The residual syrup is azeotroped with toluene, dissolved in 75 ml of acetone, and treated with one equivalent of maleic acid dissolved in 50 ml of acetone. The resulting precipitate is collected and recrystallized from additional acetone to yield 3.6 g of the title compound, melting point 213°-214° C.

EXAMPLE 84

1-Phenyl-8-[[1,2,3,4-tetrahydro-1-(n-decanoyloxy)-2-naphthalenyl]methyl]-1,3,8-triazaspiro[4.5]decan-4-one 1-Phenyl-8-[(1,2,3,4-tetrahydro-1-hydroxy-2-naphthalenyl)methyl]-1,3,8-triazaspiro[4.5]decan-4-one (0.15 mole) is dissolved in 50 ml of dry pyridine and treated with 3.0 g of n-decanoyl chloride. The resulting solution is stirred under a nitrogen atmosphere for 16 hours. The mixture is then poured into 400 ml of ice-water and the resulting suspension is stirred for 1 hour. Extraction with methylene chloride followed by washing the organic extracts with saturated sodium bicarbonate solution, drying over anhydrous sodium sulfate, and concentration in vacuo yields the title compound.

EXAMPLES 85–112

Method A

The compound listed in column I (0.01 mole) is added to 25 ml of anhydrous pyridine and treated with 12 ml of acetic anhydride. The mixture is stirred at room temperature, poured into 400 ml of an ice-water mixture and stirred for 45 minutes. The aqueous suspension is extracted several times with methylene chloride. The combined organic extracts are dried over anhydrous sodium sulfate, filtered and the solvent is removed to yield the compound listed in column II.

Method B

Powdered calcium hydride (4.3 g) and 43 ml of acetic anhydride are combined and refluxed under a nitrogen atmosphere for 1 hour. The resulting mixture is cooled to room temperature and diluted with 15 ml of dry benzene. A mixture of the compound listed in column I (0.02 mole) in 15 ml of benzene is added dropwise. The reaction mixture is refluxed for 16 hours, poured onto 200 g of ice, stirred for 1 hour with sodium bicarbonate solution, and extracted with ether. The ether extracts are dried over anhydrous sodium sulfate and concentrated in vacuo to yield the compound listed in column II.

| Example | Column I | Column II |
|---|---|---|
| 85 | 3-methyl-1-phenyl-8-[(1,2,3,4-tetrahydro-6-chloro-1-hydroxy-2-naphthalenyl)methyl]-1,3,8-triazaspir[4.5]decan-4-one | 3-methyl-1-phenyl-8-( (1,2,3,4-tetrahydro6-chloro-1-acetoxy-2-naphthalenyl)methyl]-1,3,8-triazaspiro[4.5]decan-4-one |
| 86 | 1-phenyl-3-(2-propenyl)-8-[(1,2,3,4-tetrahydro-6-(trifluoromethyl)-1-hydroxy-2-naphthalenyl)methyl]-1,3,8-triazaspiro[4.5]decan-4-one | 1-phenyl-3-(2-propenyl)-8-[(1,2,3,4-tetrahydro-6-(trifluoromethyl)-1-acetoxy-2-naphthalenyl) methyl]-1,3,8-triazaspiro[4.5]decan-4-one |
| 87 | 1-phenyl-8-[(1,2,3,4-tetrahydro-6-methylthio-1-hydroxy-2-naphthalenyl)methyl]-1,3,8-triazaspiro( 4.5]decan-4-one | 1-phenyl-8-[(1,2,3,4-tetrahydro-6-methylthio-1-acetoxy-2-naphthalenyl)methyl]-1,3,8-triazaspiro[4.5]decan-4-one |
| 88 | 1-phenyl-8-[182,3,4-tetrahydro-6-methyl-1-hydroxy-2-naphthalenyl)methyl]-1,3,8-triazaspiro[4.5]decan-4-one | 1-phenyl-8-( (1,2,3,4-tetrahydro-6-methyl-1-acetoxy-2-naphthalenyl)methyl]-1,3,8-triazaspiro( 4.5]decan-4-one |
| 89 | 1-(4-chlorophenyl)-8-[(1,2,3,4-tetrahydro-6-ethyl-1-hydroxy-2-naphthalenyl)methyl]-1,3,8-triazaspiro[4.5]decan-4-one | 1-(4-chlorophenyl)-8-[(1,2,3,4-tetrahydro-6-ethyl-1-acetoxy-2-naphthalenyl)methyl]-1,3,8-triazaspiro[4.5]decan-4-one |
| 90 | 1-(4-fluorophenyl)-8-[(1,2,3,4-tetra hydro-6,7-dimethoxy-1-hydroxy-2-naphthalenyl)methyl]-1,3,8-triazaspiro[4.5]decan-4-one | 1-(4-fluorophenyl)-8-[(1,2,3,4-tetrahydro-6,7-dimethoxy-1-acetoxy-2-naphthalenyl)methyl]-1,3,8-triazaspiro[4.5]decan-4-one |
| 91 | 1-(4-methylphenyl)-8-[(1,2,3,4-tetrahydro-6,7-dimethyl-1-hydroxy-2-naphthalenyl)methyl]-1,3,8-triazaspiro[4.5]decan-4-one | 1-(4-methylphenyl)-8-[(1,2,3,4-tetrahydro-6,7-dimethyl-1-acetoxy-2-naphthalenyl)methyl] -1,3,8-triaza spiro[4.5]decan-4-one |
| 92 | 8-[(2,3-dihydro-5-fluoro-1-hydroxy-1H-inden-2-yl)methyl]-1-phenyl-1,3,8-triazaspiro[4.5]decan-4-one | 8-[(2,3-dihydro-5-fluoro-1-acetoxy-1H-inden-2-yl)methyl]-1-phenyl-1,3,8-triazaspiro[4.5]decan-4-one |
| 93 | 8-[(2,3-dihydro-5-chloro-1-hydroxy-1H-inden-2-yl)methyl]-1-phenyl-1,3,8-triazaspiro[4.5]decan-4-one | 8-[(2,3-dihydro-5-chloro-1-acetoxy-1H-inden-2-yl)methyl]-1-phenyl-1,3,8-triazaspiro[4.5]decan-4-one |
| 94 | 8-[(2,3-dihydro-5-ethylthio-1-hydroxy-1H-inden-2-yl)methyl) -1-phenyl-1,3,8-triazaspiro[4.5]decan-4-one | 8-[(2,3-dihydro-5-ethylthio-1-acetoxy-1H-inden-2-yl)methyl]-1-phenyl-1,3,8-triazaspiro( 4.5]decan-4-one |
| 95 | 8-[(2,3-dihydro-5-ethyl-1-hydroxy-1H-inden-2-yl)methyl]-1-phenyl-1,3,8-triazaspiro[4.5]decan-4-one | 8-[(2,3-dihydro-5-ethyl-1-acetoxy-1H-inden-2-yl)methyl]-1-phenyl-1,3,8-triazaspiro[4.5]decan-4-one |
| 96 | 8-( (2,3-dihydro-5-(trifluoromethyl)-1-hydroxy-1H-inden-2-yl)-methyl]-1-phenyl-1,3,8-triazaspiro[4.5]decan-4-one | 8-( (2,3-dihydro-5-(trifluoromethyl)-1-acetoxy-1H-inden-2-yl)methyl]-1-phenyl 1,3,8-triazaspiro[4.5]decan-4-one |
| 97 | 8-[(2,3-dihydro-1-hydroxy-1H-inden-2-yl)methyl]-3-ethyl-1-phenyl-1,3,8-triazaspiro[4.5]decan-4-one | 8-[(2,3-dihydro-1-acetoxy-1H-inden-2-yl)methyl]-3-ethyl-1-phenyl-1,3,8-triazaspiro[4.5]decan-4-one |
| 98 | 8-[(2,3-dihydro-1-hydroxy-1H-inden-2-yl)methyl]-3-propyl-1-phenyl-1,3,8-triazaspiro[4.5]decan-4-one | 8-[(2,3-dihydro-1-acetoxy-1-H-inden-2-yl)methyl]-3-propyl-1-phenyl-1,3,8-triazaspiro[4.5]decan-4-one |
| 99 | 8-[(2,3-dihydro-1-hydroxy-1H-inden-2-yl)methyl]-1-(4-chlorophenyl)-1,3,8-triazaspiro[4.5]decan-4-one | 8-[(2,3-dihydro-1-acetoxy-1H-inden-2-yl)methyl]-1-(4-chlorophenyl)-1,3,8-triazaspiro[4.5]decan-4-one |
| 100 | 8-[(2,3-dihydro-1-hydroxy-1H-inden-2-yl)methyl]-1-(4-ethylphenyl)-1,3,8-triazaspiro[4.5]decan-4-one | 8-[(2,3-dihydro-1-acetoxy-1H-inden-2-yl)methyl]-1-(4-ethylphenyl)-1,3,8-triazaspiro[4.5]decan-4-one |
| 101 | 1-phenyl-8-[(6,7,8,9-tetrahydro-5-hydroxy-benzocyclohepten-6-yl)methyl]-1,3,8-triazaspiro[4.5]decan-4-one | 1-phenyl-8-[(6,7,8,9-tetrahydro-5-acetoxy-benzocyclohepten-6-yl)methyl]-1,3,8-triazaspiro[4.5]decan-4-one |
| 102 | 1-phenyl-8-[(6,7,8,9-tetrahydro-2-chloro-5-hydroxy-benzocyclohepten-6-yl)methyl]-1,3,8-triazaspiro[4.5]decan-4-one | 1-phenyl-8-[(6,7,8,9-tetrahydro-2-chloro-5-acetoxy-benzocyclohepten-6-yl)methyl]-1,3,8-triazaspiro[4.5]decan-4-one |
| 103 | 1-phenyl-8-[(6,7,8,9-tetrahydro-2-bromo-5-hydroxy-benzocyclohepten-6-yl)methyl]- | 1-phenyl-8-[(6,7,8,9-tetrahydro-2-bromo-5-acetoxy-benzocyclohepten-6-yl)methyl]- |

-continued

| Example | Column I | Column II |
|---|---|---|
| | 1,3,8-triazaspiro[4.5]decan-4-one | 1,3,8-triazaspiro[4.5]decan-4-one |
| 104 | 1-phenyl-8-( (6,7,8,9-tetrahydro-2-fluoro-5-hydroxy-benzocyclohepten-6-yl)methyl]-1,3,8-triazaspiro[4.5]decan-4-one | 1-phenyl-8-[(6,7,8,9-tetrahydro-2-fluoro-5-acetoxy-benzocyclohepten-6-yl)methyl]-1,3,8-triazaspiro[4.5]decan-4-one |
| 105 | 1-phenyl-8-[(6,7,8,9-tetrahydro-2-methoxy-5-hydroxy-benzocyclohepten-6-yl)-methyl]-1,3,8-triazaspiro( 4.5]-decan-4-one | 1-phenyl-8-[(6,7,8,9-tetrahydro-2-methoxy-5-acetoxy-benzocyclohepten-6-yl)-methyl]-1,3,8-triazaspiro[4.5]decan-4-one |
| 106 | 1-phenyl-8-[(6,7,8,9-tetrahydro-2-(tri-fluoromethyl)-5-hydroxy-benzocyclo-hepten-6-yl)methyl]-1,3,8-triazaspiro-[4.5]decan-4-one | 1-phenyl-8-[(6,7,8,9-tetrahydro-2-(tri-fluoromethyl)-5-acetoxy-benzocyclo-hepten-6-yl)-methyl]-1,3,8-triazaspiro-[4.5]decan-4-one |
| 107 | 1-phenyl-8-[(6,7,8,9-tetrahydro-2,3-di-methoxy-5-hydroxy-benzocyclohepten-6-yl)methyl]-1,3,8-triazaspiro[4.5]decan-4-one | 1-phenyl-8-[(6,7,8,9-tetrahydro-2,3-di-methoxy-5-acetoxy-benzocyclohepten-6-yl)methyl]-1,3,8-triazaspiro[4.5]decan 4-one |

EXAMPLE 113
8-[(3,4-Dihydro-2-naphthalenyl)methyl]-1-phenyl-1,3,8-triazaspiro[4.5]decan-4-one, and the hydrochloride salt thereof

Method 1

A. 8-[(3,4-Dihydro-2-naphthalenyl)methyl]-1-phenyl-1,3,8-triazaspiro[4.5]decan-4-one 1-Phenyl-8-[(trans-1,2,3,4-tetrahydro-1-hydroxy-2-naphthalenyl)methyl]-1,3,8-triazaspiro[4.5]decan-4-one (1:1) (10g, see example 3) is added in small portions to an acid mixture comprising 60 ml acetic acid containing 20% v/v sulfuric acid at 25° C with vigorous stirring. The resulting light-brown solution is stirred for 16 hours protected from moisture by a drying tube. The reaction mixture is then warmed gently on a steam bath for 5 minutes, poured warm into ice water, neutralized with solid sodium bicarbonate, and extracted with chloroform. Concentration of the dried chloroform solution and trituration with ether give 7.4 g (78%) of pure, colorless olefin product, melting point 205°–206° C.

B. 8-[(3,4-Dihydro-2-naphthalenyl)methyl]-1-phenyl-1,3,8-triazaspiro [4.5]decan-4-one, hydrochloride (1:1)

Finely-ground free base olefin (6 g) of part A is slurried in absolute ethanol (250 ml) and treated with ethereal hydrogen chloride (5.9 ml of 3.3 N ethereal hydrogen chloride is a 20% excess). The reaction mixture becomes clear, and cooling in the freezer produces 5.8 g (88%) of the title compound in the form of white needles, melting point 262°–263° C.

Method 2

A. 8-[(3,4-Dihydro-2-naphthalenyl)methyl]-1-phenyl-1,3,8-triazaspiro [4.5]decan-4-one A mixture comprising 5.0 g of 1-phenyl-8-[(trans-(1,2,3,4-tetrahydro-1-hydroxy-2-naphthalenyl) methyl]-1,3,8-triazaspiro[4.5]decan-4-one, hydrochloride (1:1) (see example 4) 25 ml acetic acid and 0.5 g p-toluenesulfonic acid monohydrate is refluxed for one hour under nitrogen and the hot solution is poured onto 200 g ice. This acid solution is basified with addition of solid sodium bicarbonate. The resulting suspension is extracted with methylene chloride and the combined organic extracts are washed with water, dried, and concentrated giving 4.1 g (86%) of crude olefin. Crystallization of this material from ethyl acetate/ether gives colorless plates, melting point 205°–206° C.

B. 8-[(3,4-Dihydro-2-naphthalenyl)methyl]-1-phenyl-1,3,8-triazaspiro[4.5]decan-4-one, hydrochloride (1:1)

The crystalline spiro-olefin of part A (2.0 g) is suspended in 75 ml of absolute ethanol and treated with 4.0 ml of 3.3N ethanolic hydrogen chloride. The mixture becomes clear and cooling overnight produces 2.1 g of the title compound in the form of a white, crystalline powder, melting point 262°–263° C.

Method 3

A. 3,4-Dihydro-2-chloromethyl naphthalene

This chloromethyl compound is prepared according to the procedure described by F. Petru and J. Rehor, Chem. Listy, 52, 353–355 (1958). In a 1-liter flask equipped with a dropping funnel and a condenser with drying tube is placed paraformaldehyde (8.0 g) and concentrated hydrogen chloride (275 ml). The resulting mixture is placed in a 90° C constant temperature oil bath and stirred for 10 minutes. Dihydronaphthalene (43.0 g of 75% technical grade) is then added dropwise to the acid solution over a 15-minute period. The reaction mixture is vigorously stirred at 90° C for 4 hours, cooled, and diluted with water (75 ml). The oil that separates is collected by extraction with ether. The ether extracts are neutralized with sodium bicarbonate solution, dried, and concentrated to give a yellow liquid. Fractional distillation at 98°–101° C at 1.4 mm of Hg provides 22.1 g (50%) of the chloromethyl compound.

B. 8-[(3,4-Dihydro-2-naphthalenyl)methyl]-1-phenyl-1,3,8-triazaspiro[4.5]decan-4-one A mixture of 1-phenyl-1,3,8-triazaspiro[4.5]decan-4-one (5.0g), 3,4-dihydro-2-chloromethylnaphthalene (3.8 g), and powdered sodium carbonate (3.4 g) in toluene (200 ml) containing several crystals of iodine is refluxed for 14 hours with vigorous stirring under nitrogen. The reaction mixture is then cooled, diluted with methylene chloride (100 ml), and filtered. The filtrate is concentrated and the crude product triturated with ether (100 ml) to give a crude yellow solid. Chromatography of this material using a short silica gel column with ethyl acetate/hexane (3:1) produces 4.7 g (60%) of pure, free base olefin, melting point 205°–206° C.

Method 4

A. 1-[(3,4-Dihydro-2-naphthalenyl)methyl]-4-anilino isonipecotamide

A mixture of 4-anilino isonipecotamide (5.5 g), 3,4-dihydro-2-chloromethylnaphthalene (4.0 g), and powdered sodium carbonate (3.5 g) in toluene (200 ml) containing several crystals of iodine is refluxed for 14 hours with vigorous stirring under nitrogen. The reaction mixture is then cooled, diluted with methylene chloride (100 ml), and filtered. The filtrate is concentrated and the crude product triturated with ethyl acetate (100 ml) to give the title compound.

B. 8-[(3,4-Dihydro-2-naphthalenyl)methyl]-1-phenyl-1,3,8-triazaspiro[4.5]decan-4-one A mixture of 1-[(3,4-dihydro-2-naphthalenyl)methyl]-4-anilino isonipecotamide (5.0 g) and formamide (18 g) is heated for 12 hours at 170° C. The reaction mixture is cooled, diluted with water (100 ml), and extracted with chloroform. The chloroform solution is dried over sodium sulfate and concentrated to give crude product. Trituration with ethyl acetate produces the title compound.

Method 5

A. 1-[(3,4-Dihydro-2-naphthalenyl)methyl]-4-anilino isonipecotamide

A mixture of 1-[(3,4-dihydro-2-naphthalenyl)methyl]-4-anilino isonipecotonitrile (5.0 g) and 90% sulfuric acid (60.0 g) is heated for 10 minutes at 70° C. The mixture is then stirred at room temperature for an additional hour. The reaction mixture is poured into ice-water, basified with ammonium hydroxide, and extracted with chloroform. Concentration of the dried chloroform solution followed by trituration with benzene yields the title compound.

B. 8-[(3,4-Dihydro-2-naphthalenyl)methyl]-1,3,8-triazaspiro-[4.5]dec-2-en-4-one

A mixture of 1-[(3,4-dihydro-2-naphthalenyl)methyl]-4-anilino isonipecotamide (6.0 g), triethyl orthoformate (3.0 g), toluene (30 ml), and glacial acetic acid (1.5 ml) is refluxed under nitrogen for 38 hours. The reaction mixture is cooled and poured into aqueous ammonium hydroxide. The organic layer is separated, dried, and concentrated to give the crude product. Digestion of this material with benzene followed by filtration and concentration of the organic solution yields the title compound.

C. 8-[(3,4-Dihydro-2-naphthalenyl)methyl]-1-phenyl-1,3,8-triazaspiro[4.5]decan-4-one A solution of 8-[(3,4-dihydro-2-naphthalenyl)methyl]-1,3,8-triazaspiro[4.5]dec-2-en-4-one (5.0 g) in dry tetrahydrofuran (30 ml) is added dropwise to a slurry of lithium aluminum hydride (0.5 g) in tetrahydrofuran (60 ml). The resulting mixture is refluxed under nitrogen for 16 hours. The reaction mixture is cooled and treated, in order, with water (0.6 ml), 15% sodium hydroxide solution (0.6 ml), and water (1.8 ml). The resulting mixture is stirred for 30 minutes. The mixture is filtered and the solids washed with chloroform. The filtrate is washed with brine, dried over sodium sulfate, and concentrated to give the title compound.

Method 6

A. 1-[(3,4-Dihydro-2-naphthalenyl)methyl]-4-oxopiperidine

A mixture of 4-piperidone (2.2 g), 3,4-dihydro-2-chloromethylnaphthalene (4.0 g), and powdered sodium carbonate (3.5 g) in tolune (200 ml) containing several crystals of iodine is refluxed for 14 hours with vigorous stirring under nitrogen. The reaction mixture is then cooled, diluted with methylene chloride (100 ml), and filtered. The filtrate is concentrated and the crude product triturated with 1:1 hexane/ether (100 ml) to give the title compound.

B. 1-[(3,4-Dihydro-2-naphthalenyl)methyl]-4-anilino isonipecotonitrile

A mixture of 1-[(3,4-dihydro-2-naphthalenyl)methyl]-4-oxopiperidine (24.0 g), aniline (9.3 g), and glacial acetic acid (70 ml) is cooled to 30° C and heated with a solution of potassium cyanide (7.2 g) in water (20 ml). The resulting mixture is stirred for 16 hours at room temperature. The reaction mixture is poured into aqueous ammonium hydroxide and extracted with chloroform. The organic solution is dried and concentrated to give the title compound.

C. 8-[(3,4-Dihydro-2-naphthalenyl)methyl]-1-phenyl-1,3,8-triazaspiro[4.5]decan-4-one Conversion of 1-[(3,4-dihydro-2-naphthalenyl)methyl]-4-anilino isonipecotonitrile to the title compound can be accomplished using procedures described in methods 4 and 5.

Method 7

A. 1-[(1,2,3,4-tetrahydro-1-oxo-2-naphthalenyl)methyl]-4-anilino isonipecotamide 2-[(Dimethylamino)methyl]-3,4-dihydro-1(2H)-naphthalenone, hydrochloride (10.0 g) and 4-anilino isonipecotamide (10.2 g) are dissolved in absolute ethanol (150 ml) by brief heating. The reaction mixture is stirred at room temperature under nitrogen for 16 hours. The resulting precipitate is collected by filtration, washed with additional absolute ethanol, and dried in vacuo to give the title compound.

B. 1-[(1,2,3,4-tetrahydro-1-oxo-2-naphthalenyl)methyl]-4-anilino isonipecotamide, hydrochloride (1:1)

Finely-ground 1-[(1,2,3,4-tetrahydro-1-oxo-2-naphthalenyl)-methyl]-4-anilino isonipecotamide (5.0 g) is slurried in absolute ethanol and treated with 1.2 equivalents of ethereal hydrogen chloride. The resulting mixture is cooled and filtered to yield the title compound.

C. 1-[(1,2,3,4-tetrahydro-1-hydroxy-2-naphthalenyl)-methyl]-4-anilino isonipecotamide Finely-ground 1-[(1,2,3,4-tetrahydro-1-oxo-2-naphthalenyl)-methyl]-4-anilino isonipecotamide, hydrochloride (1:1) (5.0 g) is slurried in methanol (100 ml) and cooled in ice. To this mixture is added an aqueous solution of sodium borohydride (3.0 g) in water (25 ml). The resulting mixture is stirred for 15 hours at room temperature under nitrogen. Dilution of the reaction mixture with water (200 ml), extraction with methylene chloride, and concentration of the dried organic solution give the title compound.

D. 8-[(3,4-Dihydro-2-naphthalenyl)methyl]-1-phenyl-1,3,8-triazaspiro[4.5]decan-4-one A mixture of 1-[(1,2,3,4-tetrahydro-1-hydroxy-2-naphthalenyl)-methyl]-4-anilino isonipecotamide (5.0 g) and formamide (15.0 g) is treated dropwise with concentrated sulfuric acid (10.0 g). The resulting mixture is refluxed for 2 hours, cooled and poured onto ice (50 g). The aqueous mixture is basified with ammonium hydroxide and extracted with chloroform. The organic solution is dried over sodium sulfate and concentrated to give the title compound.

Method 8

A. 1-[(1,2,3,4-tetrahydro-1-oxo-2-naphthalenyl)methyl]-4-anilino isonipecotonitrile 2-[(Dimethylamino)methyl]-3,4-dihydro-1(2H)-naphthalenone, hydrochloride (10.0 g) and 4-anilino isonipecotonitrile (10.2 g) are dissolved in absolute ethanol (150 ml) by brief heating. The reaction mixture is stirred at room temperature under nitrogen for 16 hours. The resulting precipitate is collected by filtration, washed with additional absolute ethanol, and dried in vacuo to give the title compound.

B. 1-[(1,2,3,4-tetrahydro-1-oxo-2-naphthalenyl)methyl]-4-anilino isonipecotonitrile, hydrochloride (1:1)

Finely-ground 1-[(1,2,3,4-tetrahydro-1-oxo-2-naphthalenyl)-methyl]-4-anilino isonipecotonitrile (5.0 g) is slurried in absolute ethanol and treated with 1.2 equivalents of ethereal hydrogen chloride. The resulting mixture is cooled and filtered to yield the title compound.

C. 1-[(1,2,3,4-tetrahydro-1-hydroxy-2-naphthalenyl)-methyl]-4-anilino isonipecotonitrile Finely-ground 1-[(1,2,3,4-tetrahydro-1-oxo-2-naphthalenyl)-methyl]-4-anilino isonipecotonitrile, hydrochloride (1:1) (5.0 g) is slurried in methanol (100 ml) and cooled in ice. To this mixture is added an aqueous solution of sodium borohydride (3.0 g) in water (25 ml). The resulting mixture is stirred for 15 hours at room temperature under nitrogen. Dilution of the reaction mixture mixture with water (200 ml), extraction with methylene chloride, and concentration of the dried organic solution give the title compound.

D. 1-[(3,4-Dihydro-2-naphthalenyl)methyl]-4-anilino isonipecotamide

A mixture of 1-[(1,2,3,4-tetrahydro-1-hydroxy-2-naphthalenyl)-methyl]-4-anilino isonipecotonitrile (5.0 g) and 90% sulfuric acid (60.0 g) is heated for 10 minutes at 70° C. The mixture is then stirred at room temperature for an additional hour. The reaction mixture is poured into ice-water, basified with ammonium hydroxide, and extracted with chloroform. Concentration of the dried chloroform solution followed by trituration with benzene yields the title compound.

E. 8-[(3,4-Dihydro-2-naphthalenyl)methyl]-1-phenyl-1,3,8-triazaspioro[4.5]decan-4-one Conversion of 1-[(3,4-dihydro-2-naphthalenyl)methyl]-4-anilino isonipecotamide to the title compound can be accomplished using procedures described in methods 4 and 5.

EXAMPLE 114

8-[(3,4-Dihydro-6-methoxy-2-naphthalenyl)methyl]-1-phenyl-1,3,8-triazaspiro[4.5]decan-4-one A. 8-[(3,4-Dihydro-6-methoxy-2-naphthalenyl)methyl]-1-phenyl-1,3,8-triazaspiro[4.5]decan-4-one, hydrochloride (1:1)

To a suspension of 1-phenyl-8-[trans-1,2,3,4-tetrahydro-1-hydroxy-6-methoxy-2-naphthalenyl)methyl]-1,3,8-triazaspiro-[4.5]decan-4-one (4.6 g, see example 9) in ethanol (200 ml) is added ethanolic hydrogen chloride. A clear solution soon forms; then a white solid begins to precipitate. The mixture is warmed for 15 minutes on a steam bath and is then cooled producing 4.6 g (93%) of crude hydrochloride, melting point 257°-259° C. Crystallization of this product provides pure material, 3.8 g, melting point 264°-265° C.

B. 8-[(3,4-Dihydro-6-methoxy-2-naphthalenyl)methyl]-1-phenyl-1,3,8-triazaspiro[4.5]decan-4-one The above olefinic hydrochloride salt (3.8 g) is suspended in water (75 ml) and is basified with saturated sodium bicarbonate solution. The resulting mixture is extracted with methylene chloride, the methylene chloride solution dried over anhydrous sodium sulfate, and the dried solution concentrate giving the crude free base olefin as a white powder. Crystallization from cyclohexane/methylene chloride yields the title compound in the form of colorless needles, (3.0 g 84%), melting point 182°-193° C.

EXAMPLE 115

8-[(6-fluoro-1,2,3,4-tetrahydro-1-oxo-2-naphthalenyl)-methyl]-1-phenyl-1,3,8-triazaspiro[4.5]decan-4-one, hydrochloride (1:1)

A. 6-Fluoro-2-[(dimethylamino)methyl]-3,4-dihydro-1(2H)-naphthalenone, hydrochloride (1:1)

A mixture comprising 8.0 g 6-fluoro-α-tetralone, 5.3 g of dimethylamine hydrochloride, 2.0 g paraformaldehyde, and 10 ml 95% ethanol containing 0.1 ml concentrated hydrogen chloride is heated on a steam bath for 1.5 hours. The reaction mixture soon because homogeneous and the paraformaldehyde dissolves. The warm solution (bright yellow) is transferred to a widemouthed flask and is quickly diluted by the addition of acetone (100 ml). Cooling this solution in the freezer for 16 hours produced a crystalline mass of white plates that is collected and washed with additional acetone. After drying this material in vacuo, the crystalline title compound weighs 10.1 g (80%) melting point 152°-153° C.

B. 8-[(6-Fluoro-1,2,3,4-tetrahydro-1-oxo-2-naphthalenyl)-methyl]-1-phenyl-1,3,8-triazaspiro[4.5]decan-4-one, hydrochloride (1:1)

9.0 g of the product from part A dissolved in warm absolute ethanol (50 ml) and 8.0 g 1-phenyl-1,3,8-triazaspiro[4.5]-decan-4-one dissolved in hot absolute ethanol (100 ml) are combined and stirred for 16 hours at room temperature. After 2 hours, a tan precipitate begins to form. The resulting mixture is filtered and the solid collected is washed several times with additional absolute ethanol. Drying the material in vacuo yields 10.4 g. (73%) of the free base of the title compound, melting point 181°-192° C.

The free base amino ketone (10.0 g) is slurried in absolute ethanol (200 ml) and cooled in ice. This mixture is treated with 1.2 equiv. of 3.3 N ethereal hydrogen chloride. The reaction mixture is stirred at room temperature for one hour and cooled for three hours. The solid precipitate is collected by filtration and washed with additional absolute ethanol. Crystallization of this crude product from a large volume of 95% ethanol gives the title amino-ketone hydrogen chloride salt as an off-white powder (10. 1 g, 92%), melting point 193°-194° C.

EXAMPLE 116 trans-8-[(6-Fluoro-1,2,3,4-tetrahydro-1-hydroxy-2-naphthalenyl)-methyl]-1-phenyl-1,3,8-triazaspiro[4.5]decan-4-one, hydrochloride (1:1)

6.0 g of 8-[(6-fluoro-1,2,3,4-tetrahydro-1-oxo-2-naphthalenyl)methyl]-1-phenyl-1,3,8-triazaspiro[4.5]decan-4-one, hydrochloride (1:1) (see example 115) is finely-ground, slurried in methanol (150 ml) and cooled in ice. To this mixture is added an aqueous solution of sodium borohydride (2 g in 25 ml of water). The resulting mixture is stirred for 16 hours at room temperature under nitrogen. Dilution of the reaction mixture with water (200 ml), extraction with methylene chloride, and concentration give the amino-alcohol 4.8 g (87%), melting point 237°-238° C. NMR and IR analyses indicate complete reduction, while TLC analysis indicates almost all trans free base.

The finely-ground free base amino-alcohol (1.0 g) is slurried in absolute ethanol and treated with 1.2 equiv. of ethereal hydrogen chloride. The resulting mixture is heated on a steam bath for 15 minutes and cooled to yield 0.8 g (74%) of the title salt, melting point 209°-210° C.

EXAMPLE 117

8-[(6-Fluoro-3,4-dihydro-2-naphthalenyl)methyl]-1-phenyl-1,3,8-triazaspiro[4.5]decan-4-one, hydrochloride (1:1)

Finely-ground trans-8-[(6-fluoro-1,2,3,4-tetrahydro-1-hydroxy-2-naphthalenyl)methyl]-1-phenyl-1,3,8-triazaspiro[4.5]-decan-4-one (3g, see example 116) is added in small portions to a rapidly stirred acid solution comprising 20 ml acetic acid containing 20% v/v sulfuric acid maintained at 25° C. The resulting light-brown solution is stirred overnight at room temperature under nitrogen. The dehydration mixture is then gently warmed on a steam bath for 10 minutes. The warm solution is poured into ice-water (400 ml) and the resulting suspension basified with solid sodium bicarbonate. Extraction with chloroform yields a tan solid (1.9 g. 66%) containing small amounts of three impurities detected by TLC analysis. High pressure liquid chromatography (HPLC) of this material on silica gel with ethyl acetate gives 1.5 g of the free base of the title compound as colorless prisms, melting point 186°–187° C.

The free base is slurried in absolute ethanol and treated with 1.2 equivalents of ethereal hydrogen chloride. The resulting mixture is heated for 15 minutes on a steam bath and cooled to produce 1.2 g. (85%) of the title compound in the form of a white granular salt, melting point 272°–273° C.

EXAMPLE 118

8-[(6-Chloro-1,2,3,4-tetrahydro-1-oxo-2-naphthalenyl)-methyl]-1-phenyl-1,3,8-triazaspiro[4.5]decan-4-one, hydrochloride (1:1)

A. 6-Chloro-2-[(dimethylamino)methyl]-3,4-dihydro-1-(2H)-naphthalenone, hydrochloride (1:1)

A mixture comprising 6.0 g 6-chloro-α-tetralone, 3.5 g dimethylamine hydrochloride, 1.3 g paraformaldehyde, and 7 ml 95% ethanol containing 0.07 ml concentrated hydrogen chloride is heated on a steam bath for 1.5 hours. The reaction mixture soon become homogeneous and the paraformaldehyde dissolves. The warm solution is transferred to a wide-mounted flask and is quickly diluted with acetone (90 ml). Cooling this deep purpose solution in the freezer for several hours produces a crystalline mass of light purple needles that is filtered and washed with additional acetone. After drying this material in vacuum, it weighs 6.8 g (76%), melting point 137°–139° C.

B. 8-[(6-Chloro-1,2,3,4-tetrahydro-1-oxo-2-naphthalenyl)-methyl]-1-phenyl-1,3,8-triazaspiro[4.5]decan-4-one, hydrochloride (1:1)

6.0 g of the product from part A dissolved in warm absolute ethanol (40 ml) and 5.5 g 1-phenyl-1,3,8-triazaspiro[4.5]decan-4-one dissolved in hot absolute ethanol (75 ml) are combined and stirred for 16 hours at room temperature. After 3 hours, a tan precipitate begins to form. The resulting mixture is filtered and the solid collected is washed several times with additional absolute ethanol. Drying the material in vacuo yields 6.3 g (68%) of the free base title compound, melting point 179°–180° C.

The free base title compound (6.0 g) is slurried in absolute ethanol (150 ml) and cooled in ice. This mixture is treated with 1.2 equivalents of ethereal hydrogen chloride. The solid precipitate is collected by filtration and washed with additional absolute ethanol. Crystallization of this crude product from a large volume of 95% ethanol gives the title compound as a tan powder (5.7 g, 87%), melting point 194°–195° C.

EXAMPLE 119 trans-8-[(6-Chloro-1,2,3,4-tetrahydro-1-hydroxy-2-naphtahalenyl)-methyl]-1-phenyl-1,3,8-triazaspiro[4.5]decan-4-one, hydrochloride (1:1)

4.5 g of 8-[(6-chloro-1,2,3,4-tetrahydro-1-oxo-2-naphthalenyl)-methyl]-1-phenyl-1,3,8-triazaspiro[4.5]decan-4-one, hydrochloride (1:1) (see example 118) is finely ground, slurried in methanol (100 ml), and cooled in ice. To this mixture is added an aqueous solution of sodium borohydride (1.5 g sodium borohydride (4-fold molar excess) in 15 ml water). The resulting mixture is stirred for 16 hours at room temperature under a nitrogen atmosphere. Dilution of the reaction mixture with water (200ml), extraction with methylene chloride, and concentration give the amino-alchol as a tan powder, 3.4 g (81%) melting point 228–230° C. NMR and IR analyses indicate complete reduction. TLC analysis indicates the product to be almost all trans free base of the title compound.

The finely-ground free base (1.4g) is slurried in absolute ethanol (100ml) and treated with 1.2 equivalents of ethereal hydrogen chloride. The resulting mixture is heated on a steam bath for 15 minutes and cooled to give 1.2 g (79%) of the title compound, melting point 246–247° C.

EXAMPLE 120

8-[(6-Chloro-3,4-dihydro-2-naphthalenyl)methyl]-1phenyl-1,3,8-triazaspiro[4.5]decan-4-one, hydrochloride (1:1)

Finely-ground trans-8-[(6-chloro-1,2,3,4-tetrahydro-1-hydroxy-2-naphthalenyl)methyl]-1-phenyl-1,3,8-triazaspiro[4.5]-decan-4-one, hydrochloride (1:1) (3g, see example 119) is added in small portions to a rapidly stirred solution of acids comprising 20 ml acetic acid containing 20%v/v sulfuric acid. The resulting light brown solution is stirred overnight at room temperature under nitrogen. The reaction mixture is then gently warmed on a steam bath for 10 minutes. The warm solution is poured into ice-water (400ml) and the resulting suspension basified with solid soidum bicarbonate. Extraction with chloroform yields a tan solid (1.8g, 63%). HPLC purification of this material gives 1.4g of the title compound, melting point 183–184° C.

The finely-ground free base (1.2g) is slurried in absolute ethanol (100ml) and treated with 1.2 equivalents of etheral hydrogen chloride. The resulting mixture is heated for 15 minutes on a steam bath and cooled to produce 1.2g (90%) of the title salt, melting point 272–273° C.

EXAMPLE 121

8-[(5,6-Dimethoxy-3H-inden-2-yl)methyl]-1-phenyl-1,3,8-triazaspiro [4.5]decan-4-one, hydrochloride (1:1)

A suspension of 6.0 g of trans-8-[(2,3-dihydro-1-hydroxy-5,6-dimethoxy-1H-inden-2-yl)methyl]-1-phenyl-1,3,8-triazaspiro-[4.5]decan-4-one (see example 15) ethanol (150ml) is treated with ethanolic hydrogen chloride solution at room temperature. The solid material quickly dissolves forming a yellow-green solution. Several hours cooling in the freezer produces the crude hydrochloride salt as a yellow green powder (6.1g, 98%) melting point 248–250° C.

The solid hydrochloride salt (5.8g) is suspended in water (50ml) and the pH is adjusted to 8 with saturated sodium bicarbonate solution. The resulting mixture is extracted with chloroform; the chloroform solution dried over anhydrous sodium sulfate and concentrated producing a tan solid (5.2g, 98%) melting point 199-202° C. Column chromatography of the tan solid on silica gel with 1:1 ethyl acetate/chloroform gives the free base of the title compound (4.6 g, melting point 205-206° C).

The free base (4.5g) is suspended in absolute ethanol (100ml) and is treated with ethanolic hydrogen chloride. The resulting mixture is heated on a steam bath for 15 minutes and cooled overnight producing the title hydrochloride salt as a white powder (4.1 g, 84%), melting point 250-251° C.

EXAMPLES 122-177

Following the procedure of Examples 1, 3, and 113 (method 1, part A), but substituting the compound listed in column I for α-tetralone and the compound listed in column II for 1-phenyl-1,3,8-triazaspiro[4.5]decan-4-one, the compound listed in column III is obtained. In those examples utilizing a benzosuberone starting material the Mannich reaction is run in an oil bath maintained at 120° C, rather than in a steam bath.

| Example | Column II | Column II | Column III |
| --- | --- | --- | --- |
| 122 | 6-chloro-α-tetralone | 3-methyl-1-phenyl-1,3,8-triazaspiro[4.5]decan-4-one | 3-methyl-1-phenyl-8-[(3,4-dihydro-6-chloro-2-naphthalenyl)methyl]-1,3,8-triazaspiro[4.5]-decan-4-one |
| 123 | 6-(trifluoromethyl)-α-tetralone | 1-phenyl-3-(2-propenyl)-1,3,8-triazaspiro[4.5]decan-4-one | 1-phenyl3-(2-propenyl)-8-[(3,4-dihydro-6-(trifluoromethyl)-2-naphthalenyl)methyl]-1,3,8-triazaspiro(4.5]decan-4-one |
| 124 | 6-acetoxy-α-tetralone | 1-phenyl-1,3,8-triazaspiro[4.5]decan-4-one | 1-phenyl-8-[(3,4-dihydro-6-acetoxy-2-naphthalenyl)methyl]-1,3,8-triazaspiro[4.5]decan-4-one |
| 125 | 6-(methylthio)-α-tetralone | 1-phenyl-1,3,8-triazaspiro[4.5]decan-4-one | 1-phenyl-8-[83,4dihydro-6-(methylthio)-2-naphthalenyl)methyl]-1,3,8-triazaspiro[4.5]decan-4-one |
| 126 | 6-methyl-α-tetralone | 1-phenyl-1,3,8-triazaspiro[4.5]decan-4-one | 1-phenyl-8-[(3,4-dihydro-6-methyl-2-naphthalenyl)methyl]-1,3,8-triazaspiro[4.5]decan-4-one |
| 127 | 6-ethyl-α-tetralone | 1-(4-chlorophenyl)-1,3,8-triazaspiro[4.5]-decan-4-one | 1-(4-chlorophenyl)-8-[(3,4-dihydro-6-ethyl-2-naphthalenyl)-methyl]-1,3,8-triazaspiro-[4.5]decan-4-one |
| 128 | 6-methyl-α-tetralone | 3-ethyl-1-phenyl-1,3,8-triazaspiro[4.5]decan-4-one | 3-ethyl-1-phenyl-8-[(3,4-dihydro-6-methyl-2-naphthalenyl)methyl]-1,3,8-triazaspiro[4.5]decan-4-one |
| 129 | 6-ethyl-α-tetralone | 1-phenyl-3-(2-propenyl)-1,3,8-triazaspiro[4.5]-decan-4-one | 1-phenyl-3-(2-propenyl)-8-[(3,4-dihydro-6-ethyl2-naphthalenyl)methyl]-1,3,8-triazaspiro[4.5]decan-4-one |
| 130 | 7-methyl-α-tetralone | 1-phenyl-1,3,8-riazaspiro[4.5]decan-4-one | 1-phenyl-8-[(3,4-dihydro-7-methyl-2-naphthalenyl)methyl]-1,3,8-triazaspiro[4.5]decan-4-one |
| 131 | 5-methyl-α-tetralone | 1-phenyl-1,3,8-triazaspiro[4.5]decan-4-one | 1-phenyl-8-[(3,4-dihydro-5-methyl-2-naphthalenyl)methyl]-1,3,8-triazaspiro[4.5]decan-4-one |
| 132 | 6-(trifluoromethyl)-α-tetralone | 3-ethyl-1-phenyl-1,3,8-triazaspiro[4.5]decan-4-one | 3-ethyl-1-phenyl-8-[(3,4-dihydro-6-(trifluoromethyl)-2-naphthalenyl)methyl]-1,3,8-triazaspiro[4.5]decan-4-one |
| 133 | 6-fluoro-α-tetralone | 1-phenyl-3-(2-propenyl)-1,3,8-triazaspiro[4.5]-decan-4-one | 1-phenyl-3-(2-propenyl)-8-[83,4-dihydro-6-fluoro-2-naphthalenyl)methyl]-1,3,8-triazaspiro[4.5]decan-4-one |
| 134 | 6-acetoxy-α-tetralone | 3-methyl-1-phenyl-1,3,8-triazaspiro[4.5]decan-4-one | 3-methyl-1-phenyl-8-[(3,4-dihydro-6-acetoxy-2-naphthalenyl)methyl]-1,3,8-triazaspiro[4.5]decan-4-one |
| 135 | 6-acetoxy-α-tetralone | 1-phenyl-3-(2-propenyl)-1,3,8-triazaspiro[4.5]decan-4-one | 1-phenyl-3-(2-propenyl)-8-[83,4-dihydro-6-acetoxy-2-naphthalenyl)methyl]-1,3,8-triazaspiro[4.5]decan-4-one |
| 136 | 6-ethoxy-α-tetralone | 3-ethyl-1-phenyl-1,3,8-triazaspiro[4.5]decan-4-one | 3-ethyl-1-phenyl-8-[(3,4-dihydro-6-ethoxy-2-naphthalenyl)methyl]-1,3,8-triazaspiro[4.5]decan-4-one |
| 137 | 6-methoxy-α-tetralone | 1-phenyl-3-(2-propenyl)-1,3,8-triazaspiro[4.5]-decan-4-one | 1-phenyl-3-(2-propenyl)-8-[(3,4-dihydro-6-methoxy-2-naphthalenyl)-methyl]-1,3,8-triazaspiro[4.5]-decan-4-one |
| 138 | 6-(methylthio)-α-tetralone | 3-methyl-1-phenyl-1,3,8-triazaspiro[4.5]decan-4-one | 3-methyl-1-phenyl-8-[(3,4dihydro-6-(methylthio)-2-naphthalenyl)methyl]-1,3,8-triazaspiro[4.5]-decan-4-one |
| 139 | 6-(ethylthio)-α-tetralone | 1-(4-chlorophenyl9-1,3,8-triazaspiro[4.5]-decan4-one | 1-(4-chlorophenyl)-8-[(3,4-dihydro-6-(ethylthio)-2-naphthalenyl)-methyl]-1,3,8-triazaspiro-[4.5]decan-4-one |
| 140 | 6-methyl-α-tetralone | 3-ethyl-1-(4-chlorophenyl)-1,3,8-triazaspiro[4.5]decan-4-one | 3-ethyl-1-(4-chlorophenyl)-8-[(3,4-dihydro-6-methyl-2-naphthalenyl)methyl]-1,3,8-triazaspiro[4.5]decan-4-one |

-continued

| Example | Column II | Column II | Column III |
|---|---|---|---|
| 141 | 7-ethyl-ζ-tetralone | 1-(3-methylphenyl)-1,3,8-triazaspiro[4.5]decan-4-one | 1-(3-methylphenyl)-8-[(3,4-dihydro-7-ethyl-2-naphthalenyl)-methyl]-1,3,8-triazaspiro[4.5]-decan-4-one |
| 142 | 6-(trifluoromethyl)-α-tetralone | 1-(3-methylphenyl)-1,3,8-triazaspiro[4.5]decan-4-one | 1-(3-methylphenyl)-8-[(3,4-dihydro6-(trifluoromethyl)-2-naphthalenyl)methyl) -1,3,8-triazaspiro-[4.5]decan-4-one |
| 143 | 6-(trifluoromethyl)-α-tetralone | 3-ethyl-1-(4-t-butylphenyl)-1,3,8-triazaspiro[4.5]decan-4-one | 3-etyl-1-(4-t-butylphenyl)-8-[(3,4-dihydro-6-(trifluoromethyl)-2-naphthalenyl)methyl]-1,3,8-triazaspiro[4.5]decan-4-one |
| 144 | 6-fluoro-α-tetralone | 1-(4-ethylphenyl)-3-(2-propenyl)-1,3,8-triazaspiro[4.5]decan-4-one | 1-(4-ethylphenyl)-3-(2-propenyl)-8-[(3,4-dihydro-6-fluoro-2-naphthalenyl)methyl]-1,3,8-triazaspiro( 4.5]decan-4-one |
| 145 | 6-acetoxy-α-tetralone | 3-methyl-1-(4-fluorophenyl)-1,3,8-triazaspiro[4.5]-decan-4-one | 3-methyl-1-(4-fluorophenyl)-8-[(3,4-dihydro-6-acetoxy-2-naphthalenyl)methyl]-1,3,8-triazaspiro[4.5]decan-4-one |
| 146 | 6-methoxy-α-tetralone | 1-(3-methylphenyl)-3-(2-propenyl)-1,3,8-triazaspiro[4.5]decan-4-one | 1-(3-methylphenyl)-3-(2-propenyl)-8-[(3,4-dihydro-6-methoxy-naphthalenyl)methyl]-1,3,8-triazaspiro[4.5]decan-4-one |
| 147 | 6,7-dimethoxy-α-tetralone | 1-(4-fluorophenyl)-1,3,8-triazaspiro[4.5]-decan-4-one | 1-(4-fluorophenyl)-8-[(3,4-dihydro-6,7-dimethoxy-2-naphthalenyl)methyl]-1,3,8-triazaspiro[4.5]decan-4-one |
| 148 | 6,7-dimethyl-α-tetralone | 1-(4-methylphenyl)-1,3,8-triazaspiro[4.5]decan 4-one | 1-(4-methylphenyl)-8-[(3,4 dihydro-6,7-dimethyl-2-naphthalenyl)methyl]-1,3,8-triazaspiro[4.5]decan-4-one |
| 149 | 6,7-dichloro-α-tetralone spiro[4.5]decan-4-one | 1-phenyl-1,3,8-triaza-6,7-dichloro-2-naphthalenyl)- | 1-phenyl-8-[(3,4-dihydro- methyl]-1,3,8-triazaspiro-[4.5]decan-4-one |
| 150 | 6,7-diacetoxy-α-tetralone | 1-phenyl-1,3,8-triazaspiro-[4.5]decan-4-one | 1-phenyl-8-[83,4-dihydro-6,7-diacetoxy-2-naphthalenyl)methyl]-1,3,8-triazaspiro[4.5]decan-4-one |
| 151 | 5-fluoro-1-indanone | 1-phenyl-1,3,8-triazaspiro-[4.5]decan-4-one | 8-[(5-fluoro-3H-inden-2-yl)methyl]-1-phenyl-1,3,8-triazaspiro[4.5]decan-4-one |
| 152 | 5-chloro-1-indanone | 1-phenyl-1,3,8-triazaspiro[4.5]decan-4-one | 8-[(5-chloro-3H-inden-2-yl)-methyl]-1-phenyl-1,3,8-triazaspiro[4.5]decan-4-one |
| 153 | 5-acetoxy-1-indanone | 1-phenyl-1,3,8-triazaspiro[4.5]decan-4-one | 8-[(5-acetoxy-3-H-inden-2-yl)-methyl]-1-phenyl-1,3,8-triazaspiro[4.5]decan-4-one |
| 154 | 5-(ethylthio)-1-indanone | 1-phenyl-1,3,8-triazaspiro[4.5]decan-4-one | 8-[(5-(ethylthio)-3H-inden-2-yl)-methyl]-1-phenyl-1,3,8-triazaspiro[4.5]decan-4-one |
| 155 | 5-ethyl-1-indanone | 1-phenyl-1,3,8-triazaspiro[4.5]decan-4-one | 8-[(5-ethyl-3H-inden-2-yl)-methyl]-1-phenyl-1,3,8-triazaspiro[4.5]decan-4-one |
| 156 | 5-(trifluoromethyl)-1-indanone | 1-phenyl-1,3,8-triazaspiro[4.5]decan-4-one | 8-[(5-trifluoromethyl)-3H-inden-2-yl)methyl]-1-phenyl-1,3,8-triazaspiro[ 4.5]decan-4-one |
| 157 | 1-indanone | 3-ethyl-1-phenyl-1,3,8-triazaspiro[4.5]-decan-4-one | 8-[(3H-inden-2-yl)methyl]-3-ethyl1-phenyl-1,3,8-triazaspiro[4,5]decan-4-one |
| 158 | 1-indanone | 3-propyl-1-phenyl-1,3,8-triazaspiro[4.5]decan-4-one | 8-[(3H-inden-2-yl)methyl]-3-propyl-1-phenyl-1,3,8-triazaspiro[4.5]decan-4-one |
| 159 | 1-indanone | 1-(4-chlorophenyl)-1,3,8-triazaspiro[4.5]decan-4-one | 8-[(3H-inden-2-yl)methyl]-1-(4-chlorophenyl)-1,3,8-triazaspiro[4.5]decan-4-one |
| 160 | 1-indanone | 1-(4-ethylphenyl)-1,3,8-triazaspiro[4.5]decan-4-one | 8-[83H-inden-2-yl)methyl]-1-(4-ethylphenyl)-1,3,8-triazaspiro[4.5]decan-4-one |
| 161 | 5-chloro-1-indanone | 3-methyl-1-phenyl-1,3,8-triazaspiro[4.5]decan-4-one | 8-[(5-chloro-3-H-inden-2-yl)-methyl])-3-methyl-1-phenyl-1,3,8-triazaspiro[4.5]decan-4-one |
| 162 | 5-acetoxy-1-indanone | 1-phenyl-3-(2-propenyl)-1,3,8-triazaspiro[4.5]-decan-4-one | 8-[(5-acetoxy-3H-inden-2-yl)-methyl] -1-phenyl-3-(2-propenyl)-1,3,8-triazaspiro[4.5]decan-4-one |
| 163 | 5-(ethylthio)-1-indanone | 3-methyl-1-phenyl-1,3,8-triazaspiro[4.5]decan-4-one | 8-[5-(ethylthio)-3H-inden-2-yl)-methyl]-3-methyl-1-phenyl-1,3,8-triazaspiro[4.5]decan-4-one |
| 164 | 5-ethyl-1-indanone | 3-ethyl-1-phenyl-1,3,8-triazaspiro[4.5]decan-4-one | 8-[(5-ethyl-3-H-inden-2-yl)methyl]-3-ethyl-1-phenyl-1,3,8-triazaspiro[4.5]decan-4-one |
| 165 | 1-benzosuberone | 1-phenyl-1,3,8-triazaspiro[4.5]decan-4-one | 1-phenyl-8-[(8,9-dihydro-7H-benzocyclohepten-6-yl)methyl]-1,3,8-triazaspiro[4.5]decan-4-one |
| 166 | 7-chloro-1-benzo- | 1-phenyl-1,3,8-triaza- | 1-phenyl-8-[(8,9-dihydro-2- |

-continued

| Example | Column II | Column II | Column III |
|---|---|---|---|
|  | suberone | spiro[4.5]decan-4-one | chloro-7H-benzocyclohepten-6-yl)-methyl]-1,3,8-triazaspiro[4.5]-decan-4-one |
| 167 | 7-bromo-1-benzo-suberone | 1-phenyl-1,3,8-triaza-spiro[4.5]decan-4-one | 1-phenyl-8-[(8,9-dihydro-2-bromo-7H-benzocyclohepten-6-yl)-methyl]-1,3,8-triazaspiro[4.5]-decan-4-one |
| 168 | 7-fluoro-1-benzosuber-one | 1-phenyl-1,3,8-triaza-spiro[4.5]decan-4-one | 1-phenyl-8-[(8,9-dihydro-2-fluoro-7H-benzocyclohepten-6-yl)-methyl]-1,3,8-triazaspiro-[4.5]decan-4-one |
| 169 | 7-acetoxy-1-benzo-suberone | 1-phenyl-1,3,8-triaza-sprio[4.5]decan-4-one | 1-phenyl-8-[(8,9-dihydro-2-acetoxy-7H-benzocyclohepten-6-yl)-methyl]-1,3,8-triazaspiro-[4.5]decan-4-one |
| 170 | 7-methoxy-1-benzo suberone | 1-phenyl-1,3,8-triaza-spiro[4.5]decan-4-one | 1-phenyl-8-[(8,9-dihydro-2-methoxy-7H-benzocyclohepten-6-yl)-methyl]-1,3,8-triazaspiro[4.5]-decan-4-one |
| 171 | 7-(trifluoromethyl)-1-benzosuberone | 1-phenyl-1,3,8-triaza-spiro[4.5]decan-4-one | 1-phenyl-8-[(8,9-dihydro-2-(trifluoromethyl)-7H-benzocyclo-hepten-6-yl)methyl]-1,3,8-triazaspiro[4.5]decan-4-one |
| 172 | 7,8-dimethoxy-1-benzosuberone | 1-phenyl-1,3,8-triaza-spiro[4.5]decan-4-one | 1-phenyl-8-[(8,9-dihydro-2,3-dimethoxy-7-H-benzocyclohepten-6-yl)methyl]-1,3,8-triazaspiro-[4.5]decan-4-one |
| 173 | 7,8-dimethyl-1-benzosuberone | 1-phenyl-1,3,8-triaza-spiro[4.5]decan-4-one | 1-phenyl-8-[(8,9-dihydro-2,3-dimethyl-7H-benzocyclohepten-6-yl)methyl]-1,3,8-triazaspiro-[4.5]decan-4-one |
| 174 | 1-benzosuberone | 1-(4-chlorophenyl)-1,3,8-triazaspiro[4.5]decan-4-one | 1-(4-chlorophenyl)-8-[(8,9-di-hydro-7H-benzocyclohepten-6-yl)-methyl]-1,3,8-triazaspiro[4.5]-decan-4-one |
| 175 | 1-benzosuberone | 1-(4-methylphenyl)-1,3,8-triazaspiro-[4.5]decan-4-one | 1-(4-methylphenyl)-8-[(8,9-di-hydro-7H-benzocyclohepten-6-yl)methyl]-1,3,8-triazaspiro-[4.5]decan-4-one |
| 176 | 1-benzosuberone | 3-(2-butenyl)-1-phenyl-1,3,8-triazaspiro[4.5]-decan-4-one | 3-(2-butenyl)-1-phenyl-8-[(8,9-dihydro-7H-benzocyclohepten-6-yl)-methyl]-1,3,8-triazaspiro-[4.5]decan-4-one |
| 177 | 1-benzosuberone | 3-methyl-1-phenyl-1,3,8-triazaspiro[4.5]decan-4-one | 3-methyl-1-phenyl-8-[(8,9-di-hydro-7H-benzocyclohepten-6-yl)-methyl]-1,3,8-triazaspiro-[4.5]decan-4-one |

EXAMPLES 178-183

The compound listed in column I (0.01 mole) is added to 30 ml of 8% methanolic potassium hydroxide, refluxed for 3 minutes under argon, cooled to room temperature and diluted with sufficient water to effect solution. Excess aqueous ammonium chloride solution is added dropwise, with stirring, and the reaction mixture is extracted several times with methylene chloride. The organic extracts are dried, filtered and evaporated to give the compound listed in column II. Thereafter, the compound listed in column II is converted to the compound of formula Id listed in column III employing the procedure of Example 3 and Example 113, method 1, part A.

| Example | Column I | Column II | Column III |
|---|---|---|---|
| 178 | 1-phenyl-8-[(1,2,3,4-tetra-hydro-6-acetoxy-1-oxo-2-naphthalenyl)methyl]-1,3,8-triazaspiro[4.5]decan-4-one | 1-phenyl-8-[(1,2,3,4-tetra-hydro-6-hydroxy-1-oxo-2-naphthalenyl)methyl]-1,3,8-triazaspiro[4.5]decan-4-one | 1-phenyl-8-[(3,4-dihydro-6-hydroxy-2-naphthalenyl)-methyl]-1,3,8-triazaspiro-[4.5]decan-4-one |
| 179 | 3-methyl-1-phenyl-8-[(1,2,-3,4-tetrahydro-6-acetoxy-1-oxo-2-naphthalenyl-methyl]-1,3,8-triazaspiro-[4.5]decan-4-one | 3-methyl-1-phenyl-8-[(1,2-3,4-tetrahydro-6-hydroxy-1-oxo-2-naphthalenyl)methyl]-1,3,8-triazaspiro[4.5]decan-4-one | 3-methyl-1-phenyl-8-[(3,4-dihydro-6-hydroxy-2-naph-thalenyl)methyl]-1,3,8-tri-azaspiro[4.5]decan-4-one |
| 180 | 1-phenyl-3-(2-propenyl)-8-[1,2,3,4-tetrahydro-6-acetoxy-1-oxo-2-naphtha-lenyl)methyl]-1,3,8-triaza-spiro[4.5]decan4-one | 1-phenyl-3-(2-propenyl)-8-[(1,2,3,4-tetrahydro-6-hydroxy-1-oxo-2-naphtha-lenyl)methyl]-1,3,8-triaza-spiro[4.5]decan-4-one | 1-phenyl-3-(2-propenyl)-8-[(3,4-dihydro-6-hydroxy-2-naphthalenyl)methyl]-1,3,8-triazaspiro[4.5]-decan-4-one |
| 181 | 1-(4-chlorophenyl)-8-[(1,2,3,4-tetrahydro-6-acetoxy-1-oxo-2-naphtha-lenyl)methyl]-1,3,8-triazaspiro[4.5]decan-4-one | 1-(4-chlorophenyl)-8-[(1,2,3,4-tetrahydro-6-hydroxy-1-oxo-2-naphtha-lenyl)methyl) -1,3,8-triaza-spiro[4.5]decan-4-one | 1-(4-chlorophenyl)-8-[(3,4-dihydro-6-hydroxy-2-naphthalenyl)methyl]-1,3,8-triazaspiro[4.5]-decan-4-one |
| 182 | 8-[(2,3-dihydro-5-acetoxy-1-oxo-1H-inden-2-yl)methyl]-1-phenyl-1,3,8-triazaspiro-1-phenyl-1,3,8-triazaspiro-[4.5]decan-4-one | 8-[(2,3-dihydro-5-hydroxy-1-oxo-1H-inden-2-yl)methyl]-1-phenyl-1,3,8-triazaspiro-1-phenyl-1,3,8-triazaspiro-[4.5]decan-4-one | 8-[(5-hydroxy-3H-inden-2-yl)methyl]-1-phenyl-1,3,8-triaza-1-phenyl-1,3,8-triaza-spiro[4.5]decan-4-one |
| 183 | 1-phenyl-8-[(6,7,8,9-tetra-hydro-2-acetoxy-5-oxo-7H-benzocyclohepten-6-yl)-methyl]-1,3,8-triazaspiro- | 1-phenyl-8-[(6,7,8,9-tetra-hydro-2-hydroxy-5-oxo-7H-benzocyclohepten-6-yl)-methyl]-1,3,8-triazaspriro- | 1-phenyl-8-( (8,9-dihydro-2-hydroxy-7H-benzocyclohepten-6-yl)methyl]-1,3,8-triaza-spiro[4.5]decan-4-one |

| Example | Column I | Column II | Column III |
| --- | --- | --- | --- |
| | [4.5]decan-4-one | [4.5]decan-4-one | |

EXAMPLE 184

8-[(6-(trifluoromethyl)-1,2,3,4-tetrahydro-1-oxo-2-naphthalenyl)-methyl]-1-phenyl-1,3,8-triazaspiro[4.5]decan-4-one, hydrochloride (1:1)

A. 2-[(Dimethylamino)methyl]-6-(trifluoromethyl)-3,4-dihydro-1 (2H)-naphthalenone, hydrochloride (1:1)

A mixture of 6-(trifluoromethyl)-1-tetralone (0.90 g), dimethylamine hydrochloride (0.42 g), paraformaldehyde (0.16 g), and 95% ethanol (2 ml) containing concentrated hydrogen chloride (0.02 ml) is heated on a steam bath for 1 ½ hours. The reaction mixture soon becomes homogeneous and the paraformaldehyde dissolves. The warm solution is diluted with acetone (15 ml) and cooled to yield the title compound as white needles (1.0 g) melting point 137°–138° C.

B. 8-[(6-(Trifluoromethyl)-1,2,3,4-tetrahydro-1-oxo-2-naphthalenyl)-methyl]-1-phenyl-1,3,8-triazaspiro[4.5]decan-4-one A mixture of the above Mannich base ketone (1.0 g) and 1-phenyl-1,3,8-triazaspiro-[4.5]decan-4-one (0.74 g) in absolute ethanol (15 ml) is warmed until all solids dissolve. The resulting solution is stirred at room temperature under nitrogen for 16 hours. The resulting precipitate is collected and washed with additional absolute ethanol to yield the title compound as a granular solid (0.72 g) melting point 159°–162° C.

EXAMPLE 185

8-[(6-(Trifluoromethyl)-1,2,3,4-tetrahydro-1-hydroxy-2-naphthal-enyl)methyl]-1-phenyl-1,3,8-triazaspiro[4.5]decan-4-one 8-[(6-(Trifluoromethyl)-1,2,3,4-tetrahydro-1-oxo-2-naphthal-enyl)methyl]-1-phenyl-1,3,8,-triazaspiro[4.5]decan-4-one, hydrochloride (1:1) (0.65 g, see example 184) is slurried in methanol (10 ml) and, with cooling, treated with a solution of sodium borohydride (0.27 g) in water (2 ml). The resulting mixture is stirred at room temperature under nitrogen for 16 hours, diluted with water (10 ml), and extracted with methylene chloride. Concentration of the dried organic solution followed by trituration with absolute ethanol yields the free base of the title alcohol as a tan powder (0.5 g), melting point 238°–240° C.

EXAMPLE 186

8-[(3,4-Dihydro-6-(trifluoromethyl)-2-naphthalenyl)-methyl]-1-phenyl-1,3,8-triazaspiro[4.5]decan-4-one, hydrochloride (1:1)

8-[(6-Trifluoromethyl)-1,2,3,4-tetrahydro-1-hydroxy-2-naphthalenyl)methyl]-1-phenyl-1,3,8-triazaspiro[4.5]decan-4-one (0.50 g, see example 185) is added in portions to a vigorously stirred solution (5 ml) of 20% v/v sulfuric acid in acetic acid. The resulting brown solution is stirred for 16 hours at room temperature protected from moisture by a drying tube. The acid solution is cooled, poured onto ice, basified with solid sodium bicarbonate, and extracted with methylene chloride. Concentration of the dried organic solution provides the crude, free base olefin. Purification of this material by high pressure liquid chromatography (silica gel, ethyl acetate/hexane) yields colorless needles (0.21 g) melting point 191°–192° C.

The above free base olefin (0.20 g) is slurried in absolute ethanol and treated with excess ethereal hydrogen chloride. The resulting mixture is warmed on a steam bath until all solids dissolve and then cooled to yield the hydrochloride salt (0.19 g) melting point 264°–265° C.

EXAMPLE 187

8-[(7-Fluoro-1,2,3,4-tetrahydro-1-oxo-2-naphthalenyl)-methyl]-1-phenyl-1,3,8-triazaspiro[4.5]decan-4-one A. 2-[(Dimethylamino)methyl]-7-fluoro-3,4-dihydro-1(2H)-naphthalenone, hydrochloride (1:1)

12.8 g of 7-fluoro-α-tetralone [prepared according to the procedure of M. Sy and G. A. Thiault, Bull. Soc. Chim., France, 1308–1315 (1965)], 7.9 g of dimethylamine hydrochloride, 4.8 g of paraformaldehyde and 0.2 ml concentrated hydrochloric acid are refluxed in 95% ethanol (25 ml) for 1 ½ hours on a steam bath. The warm solution is then diluted with acetone (100 ml) and the mixture solidifies. The solid is taken up in hot 95% ethanol (50 ml), diluted with acetone (200 ml) and the precipitates that form are filtered off and dried in vacuo at 50° C for 3–4 hours to give the crude product (8.1 g), melting point 175°–177° C.

Recrystallization of 6.0 g of crude product give 4.0 g of pure title compound melting point 181°–183° C.

B. 8-[(7-Fluoro-1,2,3,4-tetrahydro-1-oxo-2-naphthalenyl)methyl]-1-phenyl-1,3,8-traizaspiro([4.5]decan-4-one 5.0 g of 2-[(dimethylamino)methyl]-7-fluoro-3,4-dihydro-1(2H)-naphthalenone hydrochloride (1:1) and 5.85 g of 1-phenyl-1,3,8-triazaspiro[4.5]decan-4-one are suspended in absolute ehtanol (55 ml) and stirred overnight while a slow stream of nitrogen is bubbled through. The solid that forms is filtered off and washed with ether to give the title compound (7.7 g), melting point 162°–165° C.

EXAMPLE 188

8-[(7-Fluoro-1,2,3,4-tetrahydro-1-hydroxy-2-naphthalenyl)methyl]-1-phenyl-1,3,8-triazaspiro[4.5]decan-4-one 11.0 g of 8-[(7-fluoro-1,2,3,4-tetrahydro-1-oxo-2-naphthalenyl)-methyl]-1-phenyl-1,3,8-traizaspiro[4.5]decan-4-one (see example 187) is taken up in methanol (240 ml), cooled in an ice-bath and treated over a 20 minute period with 6.6 equivalents of sodium borohydride in water (58 ml). The mixture is then allowed to warm up to room temperature and stirred for 48 hours. The reaction mixture is diluted with ice-water (400 ml), stirred for 30 minutes and the precipitates that form are filtered off and dried in vacuo at 80° C to give the title compound (6.9 g), melting point 210°–212° C. The filtrate is extracted with 500 ml of methylene chloride to give another 4.3 g of crude product.

5.0 g of 8-[(7-fluoro-1,2,3,4-tetrahydro-1-hydroxy-2-naphthalenyl)methyl]-1-phenyl-1,3,8-triazaspiro[4.5]decan-4-one is added in portions to 29 ml of 20% v/v sulfuric acid/acetic acid and the mixture stirred for 16 hours at room temperature. The mixture is heated on a steam bath for 5 minutes and then poured onto 400 ml of ice-water. The resulting suspension is stirred for 10 minutes and neutralized by adding solid sodium bicarbonate. A gummy product forms which is extracted with methylene chloride. The organic extract is dried over anhydrous sodium sulfate, filtered and concentrated to give the free base of the title compound (4.1 g).

The crude free base is taken up in hot ethyl acetate (100 ml), cooled, treated with 3.4 ml (1.2 equivalents) of 3.3 N ethereal hydrogen chloride and stirred for 16 hours. The suspension is heated on a steam bath for 5-10 minutes and filtered while hot. The crude hydrochloride is taken up in 400 ml absolute ethanol, treated with activated carbon, filtered and concentrated down to 200 ml. Cooling this solution gives 1.57 g of the title compound, melting point 268°-269° C.

EXAMPLE 189

8-[(7-Chloro-1,2,3,4-tetrahydro-1-oxo-2-naphthalenyl)-methyl]-1-phenyl-1,3,8-traizaspiro[4.5]decan-4-one, hydrochloride (1:1)

A. 7-Chloro-2-[(dimethylamino)methyl]-3,4-dihydro-1(2H)-naphthalenone, hydrochloride (1:1)

7-Chloro-α-tetralone (15.0 g), 8.75 g of dimethylamine hydrochloride, 3.25 g of paraformaldehyde, and 17.5 ml of 95% ethanol containing 0.2 ml of concentrated hydrogen chloride are combined and heated on a steam bath for 2 hours. The warm solution is transferred to a wide-mouthed flask, diluted with 200 ml of acetone, and allowed to stand at room temperature for several hours. The resultant crystals are collected and crystallized from acetone/ethanol to give 10.7 g of the title compound, melting point 169°-170° C.

B. 8-[(7-Chloro-1,2,3,4-tetrahydro-1-oxo-2-naphthalenyl)methyl]-1-phenyl-1,3,8-traizaspiro[4.5]decan-4-one 7-Chloro-2-[(dimethylamino)methyl]-3,4-dihydro-1(2H)-naphthalenone, hydrochloride (1:1) (9.0 g), 7.6 g of 1-phenyl-1,3,8-triazaspiro[4.5]decan-4-one and 200 ml of absolute ethanol are warmed on a steam bath until all solids dissolve. The resulting solution is stirred at room temperature for 16 hours under nitrogen. A precipitate forms which is collected and washed with absolute ethanol to give 10.9 g of the title compound melting point 161°-163° C.

C. 8-[(7-Chloro-1,2,3,4-tetrahydro-1-oxo-2-naphthalenyl)-methyl]-1-phenyl-1,3,8-triazaspiro[4.5]decan-4-one, hydrochloride (1:1)

8-[(7-Chloro-1,2,3,4-tetrahydro-1-oxo-2-naphthalenyl)methyl]-1-phenyl-1,3,8-triazaspiro[4.5]decan-4-one (10.0 g) is slurried in 200 ml of absolute ethanol and treated with excess ethereal hydrogen chloride to give 10.1 g of hydrochloride salt, melting point 187°-190° C, resolidifying to melt at 260°-262° C.

EXAMPLE 190 trans-8-[(7-Chloro-1,2,3,4-tetrahydro-1-hydroxy-2-naphthalenyl)-methyl]-1-phenyl-1,3,8-triazaspiro[4.5]decan-4-one A slurry of 8-[(7-chloro-1,2,3,4-tetrahydro-1-oxo-2-naphthalenyl)methyl]-1-phenyl-1,3,8-triazaspiro[4.5]decan-4-one, hydrochloride (1:1) (9.0 g, see example 189) in 200 ml of methanol is treated with a solution of 3.7 g of sodium borohydride in 25 ml of water. The soldium borohydride solution is added dropwise with ice cooling. The resulting mixture is stirred for 16 hours under nitrogen at room temperature. The reaction mixture is diluted with water and extracted with methylene chloride. Concentration of the dried methylene chloride solution affords a crude semi-solid. Trituration with absolute ehtanol gives 6.4g of the title compound, melting point 248°-249° C.

EXAMPLE 191

8-[(7-Chloro-3,4-dihydro-2-naphthalenyl)methyl]-1-phenyl-1,3,8-triazaspiro[4.5]decan-4-one, hydrochloride (1:1)

A. 8-[(7-Chloro-3,4-dihydro-2-naphthalenyl)methyl]-1-phenyl-1,3,8-triazaspiro[4.5]decan-4-one trans-8-[(7-Chloro-1,2,3,4-tetrahydro-1-hydroxy-2-naphthalenyl)methyl]-1-phenyl-1,3,8-triazaspiro[4.5]decan-4-one (4.0 g, see example 190) is added in portions to 25 ml of 20% v/v sulfuric acid/acetic acid and the resulting solution is stirred for 16 hours at room temperature protected from moisture by a drying tube. The acid solution is then warmed for 5 minutes on a steam bath, cooled, poured onto 200 g of ice, and basified with solid sodium bicarbonate. The resulting mixture is extracted with methylene chloride. Concentration of the dried methylene chloride solution provides 2.3 g of a crude solid. Crystallization of this material from absolute ethanol gives 1.6 g of the title compound, melting point 191°-192° C.

B. 8-[(7-Chloro-3,4-dihydro-2-naphthalenyl)methyl]-1-phenyl-1,3,8-triazaspiro[4.5]decan-4-one, hydrochloride (1:1)

8-[(7-Chloro-3,4-dihydro-2-naphthalenyl)methyl]-1-phenyl-1,3,8-triazaspiro[4.5]decan-4-one (1.6 g) is dissolved in 100 ml of absolute ethanol and treated with excess ethereal hydrogen chloride to give the crude hydrochloride salt. The crude salt is crystallized from methanol to yield 1.4 g of the title compound, melting point 274°-275° C.

EXAMPLE 192

1-Phenyl-8-[(1,2,3,4-tetrahydro-6,7-dimethyl-1-oxo-2-naphthal-enyl)methyl]-1,3,8-triazaspiro[4.5]decan-4-one, hydrochloride (1:1)

A. 2-[(Dimethylamino)methyl]-3,4-dihydro-6,7-dimethyl-1(2H)-naphthalenone, hydrochloride (1:1)

A mixture of 10.0 g of 6,7-dimethyl-α-tetralone, 6.0 g of dimethyl amine hydrochloride, 2.2 g of paraformaldehyde, and 12 ml of 95% ethanol containing .15 ml of concentrated hydrogen chloride is heated on a steam bath for 3 hours. After the mixture has been heating for a short time, an additional 20 ml of 95% ethanol is added. The mixture is cooled, yielding a crystalline mass that is washed with absolute ethanol to give 11.5 g of the title compound, melting point 204°-205° C.

B. 1-Phenyl-8-[(1,2,3,4-tetrahydro-6,7-dimethyl-1-oxo-2naphthalenyl)methyl]-1,3,8-triazaspiro[4.5]decan-4-one A mixture of 14.0 g of 2-[(dimethylamino)methyl]-3,4-dihydro-6,7-dimethyl-1(2H)-naphthalenone, hydrochloride, 13.1 g of 92% 1-phenyl-1,3,8-triazaspiro[4.5]decan-4-one and 250 ml of absolute ethanol is warmed on a steam bath for 1 hour and then stirred vigorously for 14 hours. The resulting precipitates are collected and washed with absolute ethanol to give 17.6 g of the title compound, melting point 182°-183° C.

C. 1-Phenyl-8-[(1,2,3,4-tetrahydro-6,7-dimethyl-1-oxo-2-naphthalenyl)methyl]-1,3,8-triazaspiro[4.5]decan-4-one, hydrochloride (1:1)

1-Phenyl-8-[(1,2,3,4-tetrahydro-6,7-dimethyl-1-oxo-2-naphthalenyl)methyl]-1,3,8-triazaspiro[4.5]decan-4-one (15.0 g) is slurried in 150 ml of absolute ethanol and treated with 1.2 equivalents of ethereal hydrogen chloride. The resulting mixture is stirred at room temperature for 1 hour and then filtered to yield 14.7 g of the title compound, melting point 260°-262° C.

EXAMPLE 193 trans-1-Phenyl-8-[(1,2,3,4-tetrahydro-6,7-dimethyl-1-hydroxy-2-naphthalenyl)methyl]-1,3,8-triazaspiro[4.5]decan-4-one A slurry of 9.0 of 1-phenyl-8-[(1,2,3,4-tetrahydro-6,7-dimethyl-1-oxo-2-naphthalenyl)methyl]-1,3,8-triazaspiro[4.5]decan-4-one, hydrochloride (1:1) (see example 192) in 200 ml of methanol is treated with 3.8 g of sodium borohydride in 40 ml of water. The sodium borohydride is added dropwise with ice cooling. The resulting mixture is stirred for 16 hours under nitrogen at room temperature. The mixture is diluted with water and extracted with methylene chloride. Concentration of the dried methylene chloride solution yields a crude solid. Trituration with absolute ethanol gives 6.6 g of the title compound, melting point 232°-233° C.

EXAMPLE 194

8-[(3,4-Dihydro-6,7-dimethyl-2-naphthanlenyl)methyl]-1-phenyl-1,3,8-triazaspiro[4.5]decan-4-one, hydrochloride (1:1)

A. 8-[(3,4-Dihydro-6,7-dimethyl-2-naphthalenyl)methyl]-1-phenyl-1,3,8-triazasiro[4.5]decan-4-one trans-1-Phenyl-8-[(1,2,3,4-tetrahydro-6,7-dimethyl-1-hydroxy-2-naphthalenyl)methyl]-1,3,8-triazaspiro[4.5]decan-4-one (4.0 g, see example 193) is added in portions to 25 ml of 20% v/v sulfuric acid/acetic acid and the resulting solution is stirred for 16 hours at room temperature protected from moisture by a drying tube. The acid solution is warmed for 5 minutes on a steam bath, cooled, poured onto 200 g of ice and basified with solid sodium bicarbonate. The resulting mixture is extracted with methylene chloride. Concentration of the dried methylene chloride solution provides 2.7 g of solid. Crystallization of this material from absolute ethanol gives 2.1 g of the title compound, melting point 227°-228° C.

B. 8-[(3,4-Dihydro-6,7-dimethyl-2-naphthalenyl)methyl]-1-phenyl-1,3,8-triazaspiro[4.5]decan-4-one, hydrochloride (1:1)

8-[(3,4-Dihydro-6,7-dimethyl-2-naphthalenyl)methyl]-1-phenyl-1,3,8-triazaspiro[4.5]decan-4-one (2.1 g) in 100 ml of absolute ethanol is treated with an excess of ethereal hydrogen chloride to yield the crude salt. The title compound (2.1 g) is crystallized from methanol and has a melting point of 276°-277° C.

EXAMPLE 195

1-Phenyl-8-[(1,2,3,4-tetrahydro-7-methoxy-1-oxo-2-naphthalenyl)-methyl]-1,3,8-triazaspiro[4.5]decan-4-one, hydrochloride (1:1)

A. 2-[(Dimethylamino)methyl]-3,4-dihydro-7-methoxy-1(2$\underline{H}$)-naphthalenone, hydrochloride (1:1)

Following the procedure of example 187A, but substituting 7-methoxy-α-tetralone for 7-chloro-α-tetralone, yields the title B. 1-Phenyl-8-[(1,2,3,4-tetrahydro-7-methoxy-1-oxo-2-naphthalenyl)methyl]-1,3,8-triazaspiro[4.5]decan-4-one A mixture of 15.0 g of 2-[(dimethylamino)methyl]-3,4-dihydro-7-methoxy-1(2$\underline{H}$)-naphthalenone, hydrochloride (1:1), 13.0 g of 1-phenyl-1,3,8-triazaspiro[4.5]decan-4-one, and 250 ml of absolute ethanol is heated on a steam bath until all solids dissolve. The resulting solution is stirred for 16 hours at room temperature under nitrogen. The resulting precipitates are collected and washed with additional absolute ethanol to give 16.7 g of the title compound.

C. 1-Phenyl-8-[(b 1,2,3,4-tetrahydro-7-methoxy-1-oxo-2-naphthalenyl)methyl]-1,3,8-triazaspiro[4.5]decan-4-one, hydrochloride (1:1)

A slurry of 1-phenyl-8-[(1,2,3,4-tetrahydro-7-methoxy-1-oxo-2-naphthalenyl)methyl]-1,3,8-triazaspiro[4.5]decan-4-one in absolute ethanol is treated with a slight excess of ethereal hydrogen chloride and the resulting mixture is chilled to yield the title compound, melting point 198°-200° C.

EXAMPLE 196 trans-1-Phenyl-8-[(1,2,3,4-tetrahydro-1-hydroxy-7-methoxy-2-naphthalenyl)methyl]-1,3,8-triazaspiro[4.5]decan-4-one A slurry of 1-phenyl-8-[(1,2,3,4-tetrahydro-7-methoxy-1-oxo-2-naphthalenyl)methyl]-1,3,8-triazaspiro[4.5]decan-4-one, hydrochloride (1:1) (10.0 g, see example 195) in 150 ml of methanol is cooled in ice and treated dropwise with 4.5 g of sodium borohydride in 25 ml of water. The resulting mixture is stirred over a 60-hour period at room temperature under nitrogen. The reaction mixture is diluted with water and extracted with methylene chloride. Concentration of the dried methylene chloride solution yields the crude product. Trituration with absolute ethanol gives 8.1 g of the title compound, melting point 216°-218° C.

EXAMPLE 197

8-[(3,4-Dihydro-7-methoxy-2-naphthalenyl)methyl]-1-phenyl-1,3,8-triazaspiro[4.5]decan-4-one, hydrochloride A. 8-[(3,4-Dihydro-7-methoxy-2-naphthalenyl)methyl]-1-phenyl-1,3,8-triazaspiro[4.5]decan-4-one trans-1-Phenyl-8-[(1,2,3,4-tetrahydro-1-hydroxy-7-methoxy-2-naphthalenyl)methyl]-1,3,8-traizaspiro[4.5]decan-4-one (5.0 g, see example 196) is added in portions to 25 ml of 20% v/v sulfuric acid/acetic acid. The resulting mixture is stirred for 16 hours at room temperature protected from moisture by a drying tube. The reaction mixture is warmed on a steam bath for 5 minutes, cooled, poured onto ice, basified with solid sodium bicarbonate, and extracted with methylene chloride. The dried methylene chloride solution is concentrated to give a crude solid. Trituration with 1:1 absolute ethanol/ether yields 3.0 g of the title compound, melting point 184°-186° C.

B. 8-[(3,4-Dihydro-7-methoxy-2-naphthalenyl)methyl]-1-phenyl-1,3,8-triazaspiro[4.5]decan-4-one, hydrochloride (1:1)

A slurry of 8-[(3,4-dihydro-7-methoxy-2-naphthalenyl)-methyl]-1-phenyl-1,3,8-triazaspiro[4.5]decan-4-one (2.1 g) in 200 ml of absolute ethanol is treated with excess ethereal hydrogen chloride and cooled in a freezer. The crude salt is crystallized from a large volume of methanol to give 1.9 g of the hydrochloride salt, melting point 254°-256° C.

EXAMPLE 198

8-(1H-Inden-2-ylmethyl)-1-phenyl-1,3,8-triazas-piro[4.5]decan-4-one, hydrochloride (1:1)

A. Indene-2-carboxylic acid

Indene (29.0g) is added to a solution of chlorosulfonylisocyanate (35.4g) in ether (75ml) with mechanical stirring. The mixture is vigorously stirred for 1 hour. The solid product is collected and washed with 1:1 ether/cyclohexane to give 48.2g of material, melting point 85°-88° C. This material (35.0g) is added, with cooling, proportionwise to 50 ml of water, treated with 75 ml of 6N hydrochloric acid, and refluxed for 3 hours to give, after crystallization from absolute ethanol, 15.1g of indene-2-carboxylic acid, melting point 229°-235° C.

B. 8-(1H-Inden-2-ylcarbonyl)-1-phenyl-1,3,8-triazas-piro[4.5]-decan-4-one

Indene-2-carboxylic acid (12.8g) is dissolved in dry tetrahydrofuran (300 ml), cooled to 0° C, treated with N-methylmorpholine (40 drops), triethylamine (12 ml) and ethyl chloroformate (8.6g) and stirred for 30 minutes. To this mixture is added a suspension of 1-phenyl-1,3,8-triazaspiro[4.5]decan-4-one (20.0g) in dry tetrahydrofuran (200 ml) and the mixture is stirred at 0° C for 30 minutes. The mixture is allowed to warm to room temperature and stirred for 16 hours. The precipitated solids are filtered off, washed with additional tetrahydrofuran, and the filtrate is concentrated. The semisolid residue is dissolved in chloroform, washed with water and saturated sodium bicarbonate solution, dried, and concentrated to give the crude product.

C. 8-(1H-Inden-2-ylmethyl)-1-phenyl-1,3,8-triazaspiro[4.5]decan-4-one

Crude 8-(1H-inden-2-ylcarbonyl)-1-phenyl-1,3,8-triazaspiro-[4.5]decan-4-one (11.4g) is dissolved in dry pyridine (250 ml), treated with sodium borohydride (6.0g), and the resulting mixture is refluxed for 16 hours under a nitrogen atmosphere. The pyridine solution is cooled, poured into 2 liters of ice water, stirred for 1 hour and the precipitates filtered off. The crude product is dissolved in chloroform and washed with water and saturated sodium bicarbonate solution. Concentration of the dried chloroform solution gives a crude solid which is a mixture of compounds. Column chromatography through silica gel using ethyl acetate followed by high pressure liquid chromatography with 4:1 ethyl acetate/hexane gives 1.3g of the title compound, melting point 184°14 186° C.

D. 8-(1H-Inden-2-ylmethyl)-1-phenyl-1,3,8-triazas-piro[4.5]decan-4-one, hydrochloride (1:1)

8-(1H-Inden-2-ylmethyl)-1-phenyl-1,3,8-triazas-piro[4.5]decan-4-one (1.2g) in absolute ethanol (100 ml) is treated with 1.2 equivalents of ethereal hydrogen chloride. Cooling gives the crude hydrochloride salt which is crystallized from absolute ethanol to yield 1.1g of the title compound, melting point 264°-266° C.

What is claimed is:

1. A compound having the formula

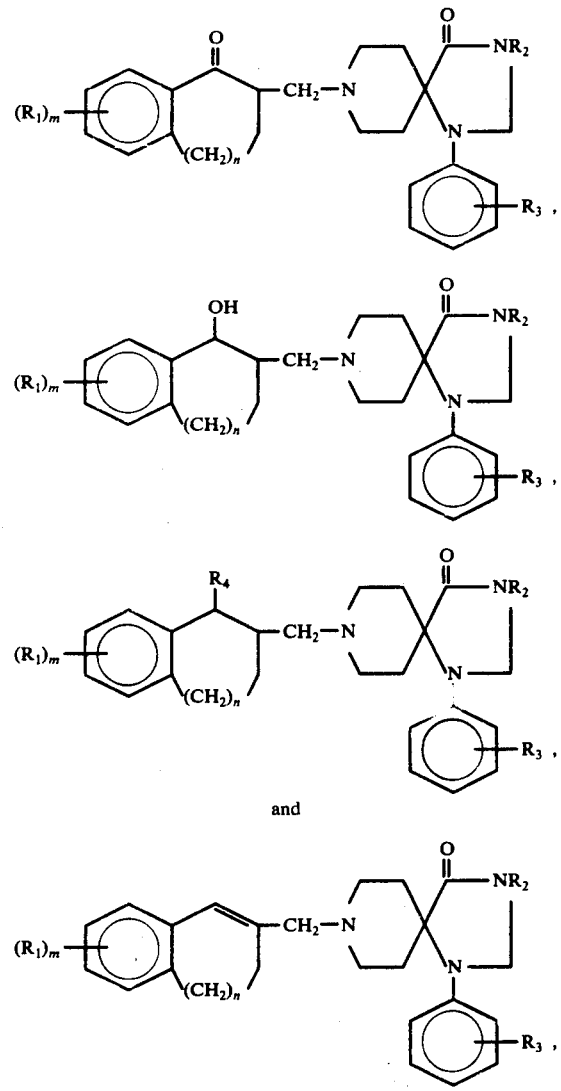

or a pharmaceutically acceptable salt thereof, wherein $R_1$ is hydrogen, halogen, hydroxy, alkanoyloxy, alkoxy, alkylthia, alkyl or trifluoromethyl; $R_2$ is hydrogen, alkyl or alkenyl having 2 to 4 carbon atoms; $R_3$ is hydrogen, halogen or alkyl; $R_4$ is formyloxy or alkanoyloxy; $m$ is 1 or 2; and $n$ is 0, 1 or 2; wherein the terms alkyl, alkoxy and alkylthio refer to groups having 1 to 10 carbon atoms and the term alkanoyloxy refers to groups having 2 to 11 carbon atoms.

2. A compound in accordance with claim 1 having the formula

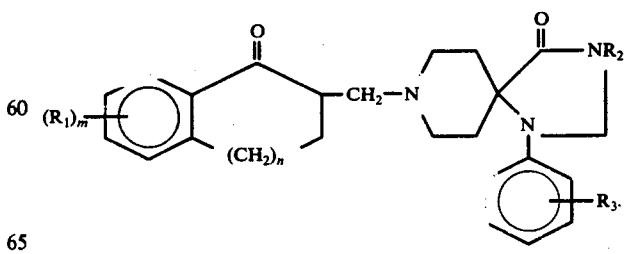

3. A compound in accordance with claim 1 having the formula

4. A compound in accordance with claim 1 having the formula

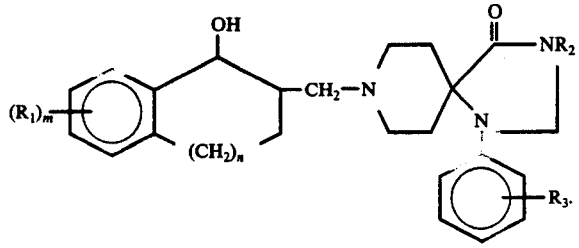

5. A compound in accordance with claim 1 having the formula

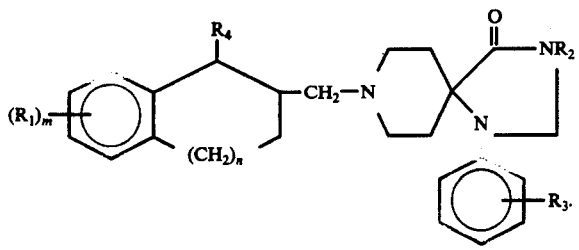

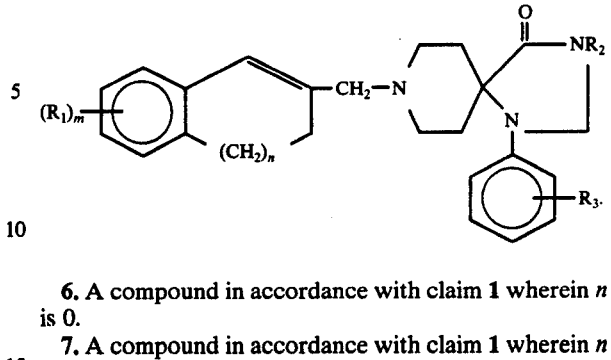

6. A compound in accordance with claim 1 wherein n is 0.

7. A compound in accordance with claim 1 wherein n is 1.

8. A compound in accordance with claim 1 wherein n is 2.

9. A compound in accordance with claim 1 wherein m is 1.

10. A compound in accordance with claim 1 wherein m is 2 and $R_1$ is alkyl or alkoxy.

11. A compound in accordance with claim 1 wherein $R_2$ and $R_3$ are hydrogen.

12. A compound in accordance with claim 1 wherein $R_1$ is hydrogen, alkyl or halogen.

13. The compound in accordance with claim 1 having the name 8-[(7-chloro-3,4-dihydro-2-naphthalenyl]-1-phenyl-1,3,8,-triazaspiro[4.5]decan-4-one or a pharmaceutically acceptable salt thereof.

14. The compound in accordance with claim 1 having the name 8-[(3,4-dihydro-2-naphthalenyl)methyl]-1-1,3,8-triazaspiro[4.5]decan-4-one or a pharmaceutically acceptable salt thereof.

15. A neuroleptic composition comprising a therapeutic amount of a compound as defined in claim 1 and a pharmaceutically acceptable carrier thereof.

16. A method of treating psychic disorders in mammalian species which comprises administering to a mammalian host a therapeutic amount of a compound as defined in claim 1.

* * * * *

UNITED STATES PATENT AND TRADEMARK OFFICE
CERTIFICATE OF CORRECTION

PATENT NO.  : 4,051,248
DATED       : September 27, 1977
INVENTOR(S) : B. Richard Vogt et al.

It is certified that error appears in the above-identified patent and that said Letters Patent are hereby corrected as shown below:

Column 1, line 54, "sails" should read -- salts --.
Example 37 (Col. III), please omit "S" from the
    end of line 2.
Example 41 (Col. III), the first line should read
    -- 1-phenyl-8-[(6,7,8,9-tetrahydro- --.
Example 41 (Col. III), in the third line "metyl]"
    should read -- methyl] --.
Example 45 (Col. II), please omit "9" at the end
    of line 1 and add --)-- in its place.
Example 46 (Col. II), please omit the entire line 3.
Example 46 (Col. III), please omit the entire line 3.
Example 54 (Col. II), in line 3 "triazasiro" should
    read -- triazaspiro --.
Example 56 (Col. II), please omit "S" at the end of
    line 4.
The second example numbered "61" should read -- 62 --.
Example 66 (Col. I), please omit the entire third line.
Example 66 (Col. II), in line 1 "hyroxy" should read
    -- hydroxy --.
Example 66 (Col. II), please add the following line 2:
    -- methyl]-1-(4-ethylphenyl)-1,3,8-triaza- --.

UNITED STATES PATENT AND TRADEMARK OFFICE
CERTIFICATE OF CORRECTION

PATENT NO. : 4,051,248
DATED : September 27, 1977
INVENTOR(S) : B. Richard Vogt et al.

It is certified that error appears in the above-identified patent and that said Letters Patent are hereby corrected as shown below:

Columns 23 and 24, please add the following examples 108-112:

| Example | Column I | Column II |
| --- | --- | --- |
| 108 | 1-phenyl-8-[(6,7,8,9-tetrahydro-2,3-dimethyl-5-hydroxy-benzocyclohepten-6-yl)methyl]-1,3,8-triazaspiro[4.5]-decan-4-one | 1-phenyl-8-[(6,7,8.9-tetrahydro-2,3-dimethyl-5-acetoxy-benzocyclohepten-6-yl)methyl]-1,3,8-triazaspiro[4.5]decan-4-one |
| 109 | 1-(4-chlorophenyl)-8-[(6,7,8,9-tetrahydro-5-hydroxy-benzocyclohepten-6-yl)methyl]-1,3,8-triazaspiro[4.5]-decan-4-one | 1-(4-chlorophenyl)-8-[(6,7,-8,9-tetrahydro-5-acetoxy-benzocyclohepten-6-yl)methyl]-1,3,8-triazaspiro[4.5]decan-4-one |
| 110 | 1-(4-methylphenyl)-8-[(6,7,8,9-tetrahydro-5-hydroxy-benzocyclohepten-6-yl)methyl]-1,3,8-triazaspiro[4.5]-decan-4-one | 1-(4-methylphenyl)-8-[(6,7,-8,9-tetrahydro-5-acetoxy-benzocyclohepten-6-yl)methyl]-1,3,8-triazaspiro[4.5]decan-4-one |
| 111 | 3-(2-butenyl)-1-phenyl-8-[(6,7,8,9-tetrahydro-5-hydroxy-benzocyclohepten-6-yl)methyl]-1,3,8-triazaspiro[4.5]-decan-4-one | 3-(2-butenyl)-1-phenyl-8-[(6,7,8,9-tetrahydro-5-acetoxy-benzocyclohepten-6-yl)methyl]-1,3,8-triazaspiro[4.5]-decan-4-one |

UNITED STATES PATENT AND TRADEMARK OFFICE
CERTIFICATE OF CORRECTION

PATENT NO. : 4,051,248
DATED : September 27, 1977
INVENTOR(S) : B. Richard Vogt et al.

It is certified that error appears in the above-identified patent and that said Letters Patent are hereby corrected as shown below:

| Example | Column I | Column II |
| --- | --- | --- |
| 112 | 3-methyl-1-phenyl-8-[(6,7,8,9-tetrahydro-5-hydroxy-benzocyclohepten-6-yl)methyl]-1,3,8-triazaspiro[4.5]-decan-4-one | 3-methyl-1-phenyl-8-[(6,7,-8,9-tetrahydro-5-acetoxy-benzocyclohepten-6-yl)-methyl]-1,3,8-triazaspiro-[4.5]-decan-4-one |

Column 27, line 61, "melting point 182°-193°C" should read -- melting point 182°-183°C --.
Column 28, line 5, "because" should read -- becomes --.
Column 28, line 29, "melting point 181°-192°C" should read -- melting point 181°-182°C --.
Column 30, line 6, "naphtahalenyl" should read -- naphthalenyl --.
Example 125 (Col. III), in the first line "[83,4dihydro" should read -- [(3,4-dihydro --.
Example 133 (Col. III), in the second line "[83,4-" should read -- [(3,4- --.
Example 135 (Col. III), in the second line "[83,4-" should read -- [(3,4- --.
Example 139 (Col. II), please omit "9" at the end of the first line.
Example 141 (Col. I), should read -- 7-ethyl-α-tetralone --.
Example 149 (Col. I), please omit line 2.
"     " (Col. II), line 2 should read -- spiro[4.5]decan-4-one --.
"     " (Col. III), line 2 should read -- 6,7-dichloro-2-naphthalenyl)- --.

UNITED STATES PATENT AND TRADEMARK OFFICE
CERTIFICATE OF CORRECTION

PATENT NO. : 4,051,248
DATED : September 27, 1977
INVENTOR(S) : B. Richard Vogt et al.

It is certified that error appears in the above-identified patent and that said Letters Patent are hereby corrected as shown below:

Example 160 (Col. III), "8-[83H-" should read
    -- 8-[(3H- --.
Example 182 (Col. III), please omit line 4.
Column 39, line 65, "soldium" should read
    -- sodium --.
Column 42, line 13, "[(b 1,2,3,4-" should read
    -- [(1,2,3,4- --.
Column 43, line 16, "proportionwise" should read
    -- portionwise --.
Column 46, Claim 14, please amend the name of the
    compound to read:
    -- 8-[(3,4-dihydro-2-naphthalenyl)methyl]-1-
      phenyl-1,3,8-triazaspiro[4.5]decan-4-one --.

Signed and Sealed this

Ninth Day of May 1978

[SEAL]

Attest:

RUTH C. MASON
Attesting Officer

LUTRELLE F. PARKER
Acting Commissioner of Patents and Trademarks